(12) United States Patent
Maurya et al.

(10) Patent No.: US 10,292,994 B2
(45) Date of Patent: May 21, 2019

(54) **BIOACTIVE FRACTIONS AND COMPOUNDS FROM *DALBERGIA SISSOO* FOR THE PREVENTION OR TREATMENT OF OSTEO-HEALTH RELATED DISORDERS**

(75) Inventors: Rakesh Maurya, Lucknow (IN); Preety Dixit, Lucknow (IN); Ritu Trivedi, Lucknow (IN); Vikram Khedgikar, Lucknow (IN); Jyoti Gautam, Lucknow (IN); Avinash Kumar, Lucknow (IN); Divya Singh, Lucknow (IN); Shelendra Pratap Singh, Lucknow (IN); Wahajuddin, Lucknow (IN); Girish Kumar Jain, Lucknow (IN); Naibedya Chattopadhyay, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 858 days.

(21) Appl. No.: 14/113,561

(22) PCT Filed: Apr. 25, 2012

(86) PCT No.: PCT/IN2012/000301
§ 371 (c)(1),
(2), (4) Date: Oct. 23, 2013

(87) PCT Pub. No.: WO2012/147102
PCT Pub. Date: Nov. 1, 2012

(65) Prior Publication Data
US 2014/0079834 A1    Mar. 20, 2014

(30) Foreign Application Priority Data

Apr. 25, 2011 (IN) .......................... 1206/DEL/2011

(51) Int. Cl.
| | |
|---|---|
| *A61K 31/7048* | (2006.01) |
| *C07D 311/36* | (2006.01) |
| *C07H 17/07* | (2006.01) |
| *A61K 31/352* | (2006.01) |
| *A61K 36/48* | (2006.01) |

(52) U.S. Cl.
CPC ........ *A61K 31/7048* (2013.01); *A61K 31/352* (2013.01); *A61K 36/48* (2013.01); *C07D 311/36* (2013.01); *C07H 17/07* (2013.01)

(58) Field of Classification Search
None
See application file for complete search history.

(56) References Cited

FOREIGN PATENT DOCUMENTS

| | | |
|---|---|---|
| FR | 2483228 A1 | 12/1981 |
| WO | WO-0062765 A2 | 10/2000 |
| WO | WO-2007042010 A2 | 4/2007 |

OTHER PUBLICATIONS

Hajare (Fitoterapia (2001), vol. 72, pp. 131-139).*
Niranjan (International Journal of Current Pharmaceutical Research (2010), vol. 2, No. 2, pp. 24-27).*
Adenusi (Afr. J. Trad. CAM (2009), vol. 6, No. 2, pp. 139-149).*
Dixit, Preety et al., "Constituents of Dalbergia sissoo Roxb. leaves with osteogenic activity", Bioorganic & Medicinal Chemistry Letters, 2012. vol. 22, No. 2.
Banerji, A. et al., "Chemical Components of the Flowers of Dalbergia sisso: Isolation of 7-Methltectorigenin, a New Isoflavone", Indian Journal of Chemistry, Jan. 1963, vol. 1. pp. 25-27.
Banerji, A. et al. "Isolation of Sissotrin, A New Isoflavone Glycoside from the Leaves of Dalbergia sissoo", Indian Journal of Chemistry, Jan. 1996, vol. 4, No. 2, pp. 70-72.
Dixit et al.; "Constituents of Dalbergia sissoo Roxb. leaves with osteogenic activity"; Bioorganic & Medicinal Chemistry Letters 22 (2012) 890-897; 4 pages.

* cited by examiner

*Primary Examiner* — Susan Hoffman
(74) *Attorney, Agent, or Firm* — Blank Rome LLP

(57) ABSTRACT

The present invention relates to bioactive fractions and compounds from *Dalbergia sissoo* for the prevention or treatment of osteo-health related disorders. The present invention relates in the field of pharmaceutical composition that provides new plant extracts, their fractions and pure compound isolated from natural sources that are useful for the prevention and/or treatment of various medical indications associated with estrogen dependent or independent diseases or syndromes or disorders preferably in the prevention or treatment of estrogen dependent or independent diseases or syndromes or disorders caused in humans and animals, and achievement of peak bone mass during skeletal growth and health in humans and animals. Particularly the present invention further relates to the processes for the preparation of biologically active extracts, fractions, and isolation of pure compounds, from *Dalbergia sissoo* plant from the family Fabaceae their pharmaceutically acceptable salts and compositions of the principal aspect of the present invention.

14 Claims, 8 Drawing Sheets

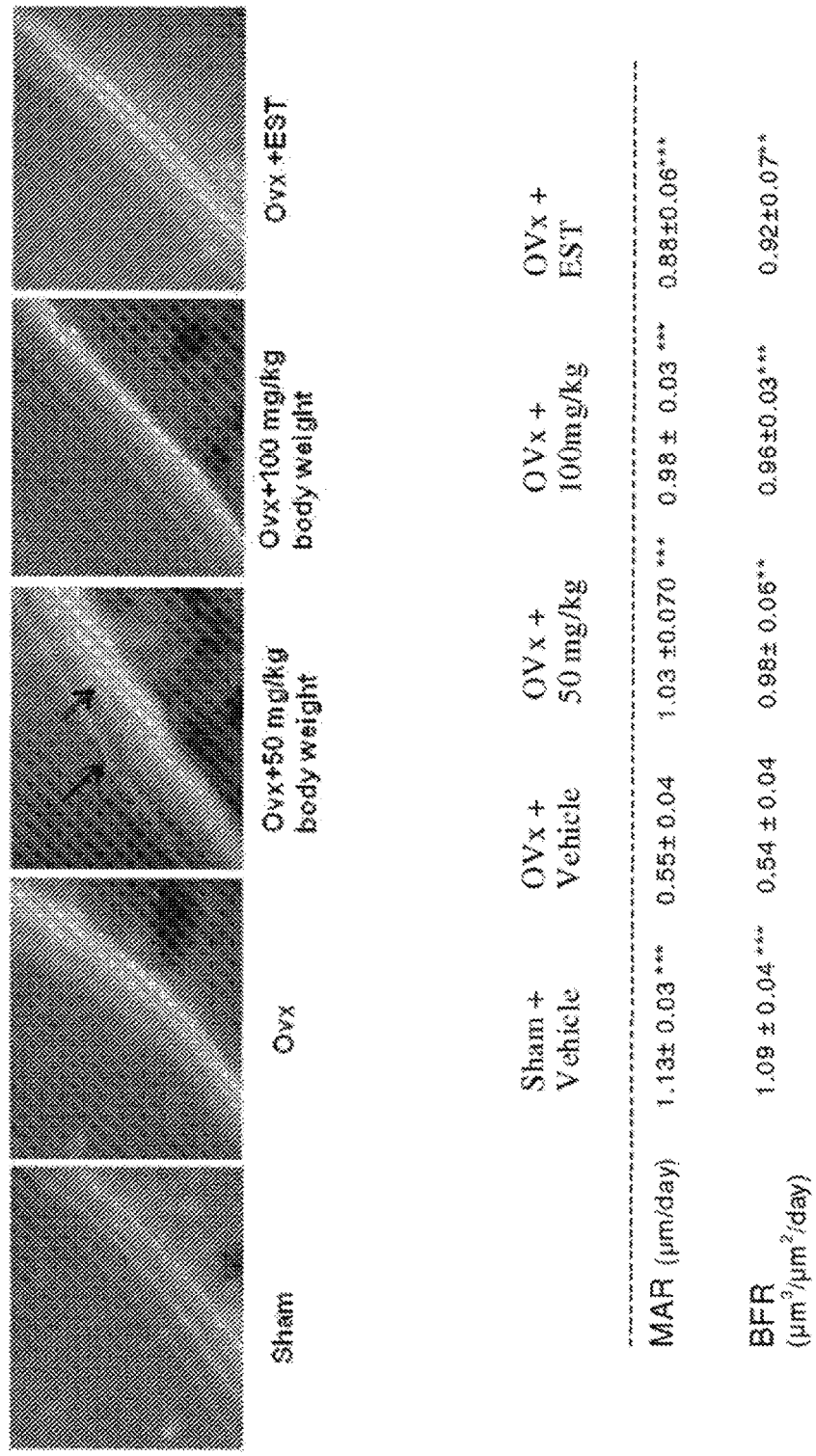

BIOACTIVE FRACTIONS AND COMPOUNDS FROM *DALBERGIA SISSOO* FOR THE PREVENTION OR TREATMENT OF OSTEO-HEALTH RELATED DISORDERS

This application is a U.S. national phase of International Application No. PCT/IN2012/000301, filed Apr. 25, 2012, which claims the priority of Indian Patent Application No. 1206/DEL/2011, filed Apr. 25, 2011, the disclosures of which are incorporated herein by reference.

FIELD OF THE INVENTION

The present invention relates to bioactive fractions and compounds from *Dalbergia sissoo* for the prevention or treatment of osteo-health related disorders. The present invention relates in the field of pharmaceutical composition that provides new plant extracts, their fractions and pure compound isolated from natural sources that are useful for the prevention and/or treatment of various medical indications associated with estrogen dependent or independent diseases or syndromes or disorders preferably in the prevention or treatment of estrogen dependent or independent diseases or syndromes or disorders caused in humans and animals, and achievement of peak bone mass during skeletal growth and health in humans and animals. Particularly the present invention further relates to the processes for the preparation of biologically active extracts, fractions, and isolation of pure compounds, from *Dalbergia sissoo* plant from the family Fabaceae their pharmaceutically acceptable salts and compositions of the principal aspect of the present invention.

BACKGROUND OF THE INVENTION

Osteoporosis, which has been defined as a "state of low bone mass" is one of the major aging problems of the society. Osteoporosis is a metabolic disorder characterized by microarchitectural deterioration of bone tissue leading to enhanced bone fragility and consequent increase in fracture risk in older members of the population. Osteoporosis fractures occur most commonly in the spine, hip, distal radius and ribs. The risk is high in women as compared to men and increases sharply after 50 years of age. Factors predisposing towards osteoporosis include family history, genetic factors, hormonal factors, inadequate nutrition, and intake of certain medications, immobility and disease. The quality of life is greatly impaired in persons with sever osteoporosis. It is known to affect >50% of women and 30% men over the age of 50 years. In women, there is also an accelerated rate of bone loss immediately and for variable number of years following menopause.

Most of the pharmacological agents available for clinical use such as calcium, vitamin D and its analogue, calcitonin, bisphosphonates, raloxifene, hormone replacement therapy (HRT) etc. act by decreasing the rate of bone resorption, thereby slowing the rate of bone loss. Timely administration of such antiresorptive agents prevents bone loss.

Hormone replacement therapy, though effective in preventing bone loss following ovariectomy or menopause in women, is associated with increased risk of endometrial hyperplasia and carcinoma [Grady, D. Grebretsadik, T. Ernestwr, V. Petitti, D. *Gynecol.* 85, 304-313 (1995), Beresford S. A. Weiss, N. S. Voigt, L. F. McKnight, B. *Lancet* 349, 458-461 (1997)], breast cancer [Riggs, L. Hartmann, L. C. *J. Med.* 348, 618-629, (2003)], and thromboembolic diseases [Delmas, P. D. *Lancet* 359, 2018-2026 (2002)].

The only side effect of calcium therapy is development of renal stones. The major disadvantage in calcitonin use is its high cost. Tachyphylaxis can develop in some individuals under calcitonin treatment. Bisphosphonates are poorly absorbed and may cause gastrointestinal irritation, diarrhea and constipation. Raloxifene has been reported to increase incidence of hot flashes, deep vein thrombosis, pulmonary embolism and leg cramps [Clemett, D.; Spencer, C. M. *Drugs* 60, 380-409 (2000)].

In view of the use of these therapies and their associated side effects indicate a need for the alternative options in the prevention and treatment of osteoporosis.

Traditional medicine is an ancient medical practice that existed in human societies before the application of modern science to health. The importance of traditional medicine as a source of primary health care was first officially recognized by the World Health Organization (WHO) in 1976 by globally addressing its Traditional Medicine Programme. In traditional medicine, there are many natural crude drugs that have the potential to treat bone diseases. However, not much laboratory work has been reported evaluating their possible development and use, except ipriflavone, a natural product derivative, which has been used clinically for such indications [Fujita, T.; Yoshikawa, S.; Ono, K.; Inoue, T.; Orimo, H. *J. Clin. Exp. Med.* 138, 113-141 (1986), Passeri, M.; Biondi, M.; Costi, D.; Bufalino, L.; Castiglione, g. N.; DiPeppe, C.; Abate, G. *Bone Miner.* 19 (Suppl. 1), S57-62 (1992)]. It is believed that herbal medicines are easily available, less expensive, and safer than chemically synthesized drugs. In India Ayurvedic medicine emerged during the rise of the philosophies of the Upanishads, Buddhism, and other schools of thought in India. Herbs played an important role in Ayurvedic medicine. In our program search for natural osteogenic plant, n-butanol soluble fraction of ethanol extract of *Dalbergia sissoo* aerial part which is renewable source exhibited osteogenic activity in our test model. Thus, the plant extract might possess bioactive ingredients that could promote bone formation. The effects on osteoporosis and total osteo-health and related disorders and has not been explored.

There is a well-recognized link between the prevalence of low peak bone mass (PBM) attainment and osteoporosis among South Asian women [Adami, S.; *Osteoporos Int, Suppl* 1, S27-30, (1994)]. PBM is defined as the highest level of bone mass achieved as a result of normal growth. Adolescence is the most critical period across the life span for bone health because more than half of PBM is accumulated during the teenage years. During these early years of life, bone formation is greater than bone resorption and the bone mass increases. PBM attained in early adult life is an important determinant of skeletal fragility at least until the age of 70 years (Ref). Following the attainment of PBM, resorption is faster than formation and the bone mass decreases. While gradual bone loss is normal to aging, it is those who fail to achieve optimal PBM and/or those with accelerated bone loss who are at the greatest risk of osteoporosis. In addition, low PBM predisposes to increased fragility fracture risk (Bonjour, J. P.; Chevalley, T.; Ferrari, S.; Rizzoli, R. *Salud Publica Mex.* 51 Suppl 1:S5-S17 (2009)].

Therefore, since individuals with a high PBM at a young age are likely to have a high bone mass in old age, agents increasing PBM during skeletal growth is a desirable goal towards prevention of osteoporosis. PBM occurs several years after the completion of linear growth as bone mineral accretion continues after this time, although the precise timing of the attainment of PBM is not certain and varies between skeletal sites. A real BMD at the femur peaks around the age of 20 yr, whereas maximum total skeletal mass occurs 6-10 yr later, well after the cessation of the anabolic action of growth hormone (GH). Factors relating to the attainment of PBM include congenital, dietary, hormonal, physical activity, lifestyle, drugs and diseases. A therapeutic intervention aimed at increasing PBM has remained limited only to controlling factors such as estrogen status, dietary calcium intake and physical activity. Calcium intake appears to be relevant up to the so-called threshold intake (1000 mg/day), but higher allowances do not seem to offer additive advantages. Exercise affects only the regions of the skeleton under mechanical stress. Estrogen administration is realistic only in conditions characterized by severe hypoestrogenism. Clearly, nutritional deficiency is one of the major reasons for lack of PBM among South Asians, particularly among females those who are much more prone to bone loss at later stages of life. Therefore, agents that promote PBM have therapeutic implication for bone loss disorders.

There is, thus, an urgent need to discover and develop a promising herbal product or a single biologically active molecule based drug or a cocktail of the pure and biologically active molecules of the plant origin that exhibit promising bone anabolic or for bone forming activity in experimental animals and human beings. The *Dalbergia sissoo* was a fit case to study and explore its true potential with respect to its bone forming response of its extract, fraction and pure biologically active marker components. The experiments have shown that its n-butanol soluble fraction and pure compounds isolated from the extract and the fraction exhibit promising bone forming activity.

*Dalbergia sissoo* Roxb. belongs to the family Fabaceae, is distributed throughout sub-Himalayan tract from Ravi to Assam ascending up to 5000 ft in India, Pakistan, Bangladesh and Afghanistan. *Dalbergia sissoo*, commonly known as "Shisham" in India, is deciduous tree, having crooked trunk and light crown [Wealth of India. Raw materials, vol 3. CSIR, New Delhi, 1950.] An aqueous extract of the leaves of *Dalbergia sissoo* has been used for the treatment of gonorrhoea [Medicinal plants of India; S. K. Jain, Roberts A. Defilipps; 1991. vol-1, 325]. Leaves of the plant are bitter and stimulant and also used as fodder. Wood of *Dalbergia sissoo* was used for leprosy [R. N. Chopra, S. L. Nayar, I. C. Chopra. Glossary of Indian Medicinal Plants, 1956, page 90].

The methylene chloride extract of the heart wood of *Dalbergia sissoo* inhibited the production of β-amyloid peptides (Aβ) so it may have therapeutic potential in the treatment of Alzheimer's disease. A compound latifolin, isolated from the crude extract of the heart wood also inhibits β-amyloid production [Ramakrishna, N. V. S., Kumar Vijaya, E. K. S., Kulkarni, A. S., Jain, A. K., Bhat, R. G., Parikh, S., Quadros, A., deuskar, N., Kalakoti, B. S., *Indian Journal of Chemistry* 40B, 539-540, 2001]. Heartwood of the plant has also been reported to have anthelmintic activity [Manandhar, N. P., *Fitoterapia* 2, 149, 1995].

The ethanolic extract of the leaves of *Dalbergia sissoo* has anti-inflammatory activity [Hajare, S. W., Chandra, S., Sharma, J., Tandan, S. K., Lal, J., Telang, A. G., *Fitoterapia* 72 (2), 131-139, 2001] and petroleum ether extract also display the same activity due to a sterol i.e. sissosterol [Abdel-Ghani, Afaf, E., Dora, Gamal A., *Mansoura journal of pharmaceutical science,* 20(1), 104-113, 2004]. It has also been reported to possess antidiabetic property in alloxan-induced diabatic rats [Niranjan, P. K., Singh, D., Prajapati, K., Jain, S. K., *International Journal of Current Pharmaceutical Science* 2(2), 24-27, 2010]. The leaves of *Dalbergia sissoo* exhibit antipyretic, analgesic properties [Hajare, S. W., Chandra, S., Tandan, S. K., Sharma, J., Lal, J., *International Journal of Pharmacology* 32, 357-360, 2000] and also acts against diarrhea [Brijesh, S., Deswani, P. G., Tetall, P., Antia, N. H., Birdl, T. J., *Indian J. Pharmocol.* 38(2), 120-124, 2006]. The preparation of *Dalbergia sissoo* leaves has been used as an alternative herbal treatment for antimicrobial property [Yadav, H., Yadav, M., Jain, S., Bhardwaj, A., Shing, V., Parkash, O., Marotta, F., *International Journal of Immunopathology and Pharmocology* 21 (4), 1013-1020, 2008]. An methanolic extract from the roots of *Dalbergia sissoo* has been reported to have anti-inflammatory activity in carrageenan-induced paw edema in rats [Kumar, S. M., Kumud, U., *Pharmacognosy journal* 2(11), 427-430, 2010]. The alcoholic extract of green branches of aerial showed a dose dependent inhibitory effect on the motility of isolated rabbit duodenum or bronchodilation and significant anti-inflammatory, antipyretic, analgesic, estrogenic activities [Sarg, T., Ateya, Abdel-Monem, Abdel-Ghani, A., Badr, W., Shams, G., *Pharmaceutical Biology* 37(1), 54-62, 1999].

The alcoholic and chloroform extract of the bark of *Dalbergia sissoo* have been reported for anti-inflammatory, anti-ulcerogenic and antioxidant activities and the compound dalbergin isolated from the bark is found to possess same activities [Khaleel, A. E., El-Gayed, S. H., Ameen, A., *Al-Azhar Journal of Pharmaceutical Sciences* 28, 285-299, 2001]. The bark has been also tested for antioxidant potential in an in vitro assay [Kumari, A., Kakkar, P., *Biomedical and Environmental sciences* 21(1), 24-29, 2008].

The anti-inflammatory, anti-ulcerogenic and antioxidant activities have been reported in alcoholic and chloroform extract of flowers of *Dalbergia sissoo* and the 7-methyltectorigenin, was found to have active constituent for these activities [Khaleel, A. E., El-Gayed, S. H., Ameen, A., *Al-Azhar Journal of Pharmaceutical Sciences* 28, 285-299, 2001].

Pure Compounds

A variety of compounds have been isolated from different parts of *Dalbergia sissoo*. The mature pod of *Dalbergia sissoo* contains isocaviunin and 7-hydroxy-4-methyl coumarin [Sharma, A., Chibber, S. S., Chawla, H. M., *Indian Journal of Chemistry* 18B, 472-473, 1979]. 4'-Rhamnoglucoside of 7-methyltectorigenin and meso-inasitol has been isolated from immature pods of *Dalbergia sissoo* [Ahluwalia, V. K., Sachdev, G. P., Seshadri, T. R., *Indian Journal of Chemistry* 3, 474, 1965]. A new isoflavane glucoside, isocaviudin among with tectoridin and caviunin 7-O-β-glucoside has been found as constituent of immature pods of *Dalbergia sissoo* [Sharma, A., Chibber, S. S., Chawla, H. M., *Indian Journal of Chemistry* 19B, 237-238, 1980]. Two isoflavone glycosides caviunin 7-O-gentiobioside and isocaviunin 7-O-gentiobioside has been isolated from the mature pods of *Dalbergia sissoo*. [Sharma, A., Chibber, S. S., Chawla, H. M., *Phytochemistry* 18, 1253, 1979; Sharma, A., Chibber, S. S., Chawla, H. M., *Phytochemistry* 19, 715, 1980].

From the flowers of *Dalbergia sissoo*, isoflavones, 7-methyltectorigenin along with tectorigenin, prunetin, kaempferol have been isolated and compound 7-methyltectorigenin has shown anti-inflammatory, anti-ulcerogenic and antioxidant activities [Banerji, A., Murti, V. V. S., Seshadri, T. R., *Indian Journal of Chemistry* 1, 25-27, 1963; Khaleel, A. E., El-Gayed, S. H., Ameen, A., *Al-Azhar Journal of Pharmaceutical Science* 28, 285-299, 2001]. Biochenin A, a potent cancer preventive agent with estrogenic activity has been isolated in good yield from the fresh flower of *Dal-* bergia sissoo [Asaab, Aya M., El-Shaer, Nagwa, S., Darwish, F., *Alexandria Journal of Pharmaceutical Science* 14(2), 103-105, 2000]. 7,4'-Dimethyltectorigenin has also been isolated from the flowers of *Dalbergia sissoo* [Banerji, A., Murti, V. V. S., Seshadri, T. R., *Current Science* 34(14), 431, 1966].

A chalcone 2,3-dimethoxy-4'-γ,γ-dimethylallyloxy-2'-hydroxychalcone, two isoflavone 7-γ,γ-dimethylallyloxy-5-hydroxy-4' methoxyisoflavone and biochenin, a flavone, 7-hydroxy-6-methoxyflavone and a rotenoid have been isolated from the root bark of *Dalbergia sissoo* [Reddy, R. V. N., Reddy, N. P., Khalivulla, S. I., Reddy, M. V. B., Gunasekar, D., Blond, A., Bodo, B., *Phytochemistry Letters* 1(1), 23-26, 2008]. The chloroform extract of bark of *Dalbergia sissoo* contain dalbergin while ethyle acetate extract shown the presence of tectorigenin, tectorigenin-7-O-apioglucoside, tectorigenin-4'-O-apioglucoside, stearic acid and palmitic acid [Ragab, A., Mostafa, S. M. I., El-Shami, I., Ibrahim, Abdel-Rahim S., *Mansoura Journal of Pharmaceutical Science* 22(2), 176-194, 2006]. Two aliphatic esters, n-hexacosan-5-ol-1-yl-propionate, n-teracosan-5-ol-yl-propionate and two pyran 7-hydroxy-8-methoxy-4-(2'-hydroxyphenyl) [4H]benzopyran, 10,12,13,trihydroxy-11-methoxyanthracenyl-15-18[2H]pyran have been isolated from ethanolic extract of stem bark of *Dalbergia sissoo* Roxb [Trag, A. R., Ali, M., Siddiqui, T. O., Mahmooduzzafar, Iqbal, M., *Journal of Saudi Chemical Society* 9(2), 341-345, 2005]. Dalbergin has significant anti-inflammatory activity, anti-ulcerogenic antioxidant activity [Khaleel, A. E., El-Gayed, S. H., Ameen, A., *Al-Azhar Journal of Pharmaceutical Science* 28, 285-299, 2001]. 4-Arylcoumarin and fisetin have also been isolated from the bark [Khaleel, A. E., El-Gayed, S. H., Ameen, A., *Al-Azhar Journal of Pharmaceutical Science* 28, 285-299, 2001]. Isotectorigenin was isolated from the bark of *Dalbergia sissoo* [Dhingra, V. K., Seshadri, T. R., Mukerjee, S. K., *Indian Journal of Chemistry* 12(10), 1118, 1974]. Dalbergenone, methyldalbergin, dalbergichromene were also known constituent of bark of *Dalbergia sissoo.*

Irisolidone, biochenin-A, muningin, tectirigenin, prunetin, genistein, sissotrin, prunetin-4-O-galactoside, norartocarpetin, β-amyrin, β-sitosterol, and stigmasterol along with 13 fatty acids were isolated from the green branches of aerial parts of *Dalbergia sissoo* Roxb [Sarg, T., Ateya, Abdel-Monem, Abdel-Ghani, A., Badr, W., Shams, G., *Pharmaceutical biology*, 37(1), 54-62, 1999].

Biochenin A, kaempferol, quercetin, kamempferol-3-O-β-D-glucoside, quercetin-3-α-L-rhamnoside, rutin, β-sitosterol were isolated from the leaves of *Dalbergia Sissoo* [Ragab, A., Mostafa, S. M. I., El-Shami, I., Ibrahim, Abdel-Rahim S., *Mansoura journal of Pharmaceutical Science* 22(2), 176-194, 2006].

The Oligosaccharides were also isolated from the leaves of *Dalbergia sissoo* [Rana, V., Kumar, V., Soli, P. L., *Carbohydrate polymers* 78(3), 520-525, 2009]. Sissosterol isolated from petroleum ether extract of *Dalbergia sissoo* leaves has also been reported to show significant antiinflmmatory activity [Abdel-Ghani, Afaf, E., Dora, Gamal A., *Mansoura journal of pharmaceutical science*, 20(1), 104-113, 2004]. Biochenin A 7-O-[β-D-apiofuranosyl-(1→6)-β-D-glucopyranoside, Biochenin A 7-O-[β-D-apiofuranosyl-(1→5)-β-D-apiofuranosyl (1→6)-β-D-glucopyranoside], tectorigenin 7-O-[β-D-apiofuranosyl(1→6)-β-D-glucopyranoside], prunetin 4'-O-[β-D-apiofuranosyl-(1→6)-β-D-glucopyranoside], 7-methyltectorigenin 4'-O-[β-D-apiofuranosyl-(1→6)-β-D-glucopyranoside], genistein 8-C-[β-D-glucopyranoside] and prunetin 4'-O-[β-D-glucopyranoside] have also been isolated from the leaves of *Dalbergia sissoo* [Farag, S. F., Ahmed, A. S., Terashima, K., Takaya, Y., Niwa, M., *Phytochemistry* 57(8), 1263-1268, 2001]. Sissotrin has been reported from the leaves [Banerji, A., Murti, V. V. S., Seshadri, T. R., *Indian Journal of Chemistry*, 4(2), 70-72, 1966].

Trunk exudates of *Dalbergia sissoo* contain S-4'-hydroxy-4-methoxy-dalbergione, S-4-methoxydelbergone, S-dalbergion, S-4-methoxydelbergiqninol, 4-[(1S)-1-phenyl-2-propenyl]-1,3-benzenediol, (4S,6S)-4-hydroxy-3-methoxy-6-(1-phenyl-2-propenyl)-2-cyclohaxene-1-one, (4S,6S)-4-hydroxy-6-(1-phenyl-2-propenyl)-2-cyclohexene-1-one, (2S,4R,5S)-4-hydroxy-5-methoxy-2-[(1S)-1-phenyl-2-propenyl)]cyclohaxanone, (2S,4R,6S)-4-hydroxy-2-methoxy-6-(1-phenyl-2-propenyl)cyclohaxanone, (1S,2S,4S,5S)-2-methoxy-5-[(1R)(1-phenyl-2-propenyl)-1,4-cyclohaxanediol, cearoin, 4-hydroxy-3-methoxy-4-(3-phenyl-2-propenyl)-2-cyclohaxen-1-one, isoliquiritigenin, butein, 2'-hydroxy-4'-methoxychalcone, hydroxyobtustyrene, (2S)-7-hydroxyflavanone, (+)-pinocembrin, plathymenin, (±)-vestitol, dihydrosepiol, formononetin, zenognosin B, 4-hydroxymedicarpin, (+)-medicarpin, (+)-vesticarpan [Shrestha, S. P., Amano, Y., Narukawa, Y., Takeda, T., *Journal of Natural Product,* 71, 98-101, 2008].

OBJECT OF THE INVENTION

One of the main object of the present invention is to provide bioactive fractions and compounds from *Dalbergia sissoo* for the prevention or treatment of osteo-health related disorders.

Another object of the present invention is to provide the crude extract derived from *Dalbergia sissoo* in pharmaceutically acceptable form in order to enhance its application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Yet another object of the present invention is to provide the n-butanol soluble fraction derived from *Dalbergia sissoo* in pharmaceutically acceptable form in order to enhance its application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Still another object of the invention is to provide individual pure compounds derived from *Dalbergia sissoo* in pharmaceutically acceptable form in order to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Yet another object of the invention is to provide a cocktail of two or more than two pure compounds derived from *Dalbergia sissoo*, in a suitable ratio or ratios, in pharmaceutically acceptable form in order to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Still another object of the present invention is to provide the n-butanol soluble fraction derived from *Dalbergia sissoo* A-4744/F004 having bone anabolic (i.e. new bone formation) effect rather than anti-resorptive (stopping further bone loss) effect.

Yet another object of the present invention is to provide, a composition devoid of uterine estrogenicity.

One more objective of the invention is to provide compounds which are non toxic to the cells.

SUMMARY OF THE INVENTION

Accordingly, the present invention provides a compound Caviunin 7-O-[β-D-apiofuranosyl-(1→6)-β-D-glucopyranoside] of formula 10 and a pharmaceutically acceptable salt thereof, Compound 10

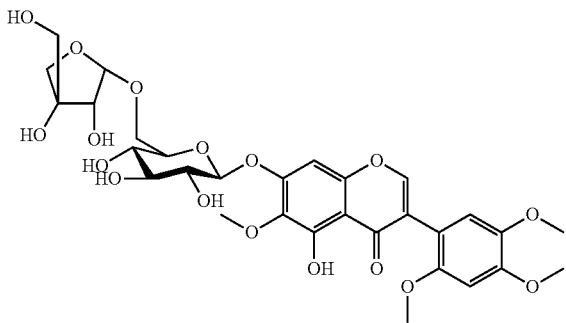

In one embodiment of the present invention, wherein the pharmaceutically acceptable salts may be selected from the group consisting of hydrochloride, formate, acetate, phenyl acetate, trifluoroacetate, acrylate, ascorbate, benzoate, chlorobenzoates, bromobezoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumerate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacate, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, toluene sulphonates.

In another embodiment of the present invention, the novel compound Caviunin 7-O-[β-D-apiofuranosyl-(1→6)-β-D-glucopyranoside] is useful for the treatment of bone disorder.

In yet another embodiment of the present invention, wherein the novel compound Caviunin 7-O-[β-D-apiofuranosyl-(1→6)-β-D-glucopyranoside] exhibits >1.0-fold increase in osteoblast differentiation over the control, assessed by ALP production.

In yet another embodiment of the present invention, wherein the novel compound Caviunin 7-O-[β-D-apiofuranosyl-(1→6)-β-D-glucopyranoside] exhibits 1.0 to 3.0-fold increase in osteoblast differentiation over the control, assessed by ALP production.

In yet another embodiment, the novel compound Caviunin 7-O-[β-D-apiofuranosyl-(1→6)-β-D-glucopyranoside] given to estrogen deficient rats induced significantly greater mineralization of the bone marrow stromal cells than the OVx rats treated with vehicle. Estrogen supplementation to OVx rats at the dose (2.5 μg/kg) that fully stimulated uterine estrogenicity, was unable to increase mineralization of the bone marrow stromal cells.

In yet another embodiment of the present invention, effective dose of novel compound Caviunin 7-O-[β-D-apiofuranosyl-(1→6)β-D-glucopyranoside] is in the range of 1 to 5 mg/kg/day.

In still another embodiment of the invention, wherein the said compound exhibits 15 fold increase in bone Morphogenic protein (BMP-2) expression in calvaria (rich in pre-osteoblasts) in rats over that of vehicle treated rats at a dose of 5.0 mg·kg$^{-1}$·day$^{-1}$ for 3 consecutive days.

In a further embodiment of the invention, wherein the compound is non toxic to the cells at concentration ranging between 1 pM to 1 μM for 48 h.

In one more embodiment of the invention, wherein the compound showed normal growth of the osteoblastic cells at concentration ranging between 1 pM to 1 μM and do not cause cell growth arrest.

In another embodiment of the invention, wherein the said compound exhibits osteogenic effect on bone marrow stromal cells at the levels ranging between 1 and 5 mg/kg/day.

In still another embodiment of the present invention, novel compound Caviunin 7-O-[β-D-apiofuranosyl-(1→6) β-D-glucopyranoside] is isolated from the leaves of plant "*Dalbergia sissoo*".

In still another embodiment of the invention, wherein said compound may be isolated from alcoholic extract A001 or bioactive fraction F004 obtained from the leaves of plant "*Dalbergia sissoo*".

A bioactive fraction F004 from the plant "*Dalbergia sissoo*" wherein the fraction comprising;
- Compound 1 Biochanin A in the range of 1.5% to 3.47%;
- Compound 2 (Caviunin 7-O-β-D-glycopyranoside)
- Compound 3 Pratensein or 3'-methoxygenistein in the range of 0.1% to 0.5%;
- Compound 4 Genstein in the range of 0.02% to 0.2%
- Compound 5 Quercetin 3-O-rutinoside in the range of 1.0% to 3.5%
- Compound 6 Biochanin 7-O-β-D-glucopyranoside in the range of 0.2% to 1.0%
- Compound 7 (Kampferol-3-O-rutinoside)
- Compound 8 (Kaempferol 3-O-β-D-glucopyranoside)
- Compound 9 (Quercetin 3-O-β-D-glucopyranoside)
- Compound 10 Caviunin 7-O-[β-D-apiofuranosyl-(1→6)-β-D-glucopyranoside in the range of 1.5% to 5.0%
- Compound 11 Biochanin A 7-O-[β-D-apiofuranosyl-(1→6)-β-D-glycopyranoside in the range of 2.0% to 5.5%
- Compound 12 Biochanin A 7-O-[β-D-apiofuranosyl-(1→5)β-D-apiofuranosyl-(1→6)-β-D-glycopyranoside in the range of 15.0% to 22.0%
- Compound 13 (Caviunin)

In an embodiment of the invention, wherein the fraction F004 significantly protects the microarchitectural features of the tibial trabecular bones of OVx rats at a dose ranging between 50 to 100 mg·kg$^{-1}$ day$^{-1}$.

Accordingly the present invention provides a process for preparation of bioactive fractions from the plant *Dalbergia sissoo*, wherein the process steps comprises:
a. powdering the leaves of the plant *Dalbergia sissoo*;
b. percolating the powder obtained in step (a) with alcohol for a period ranging between 14 to 17 hrs followed by collecting the percolate;
c. repeating the step (b) for 4 to 5 times to obtain the alcoholic extract A001;
d. fractioning the alcoholic extract as obtained in step (c) with n-hexane to obtain hexane soluble fraction and hexane insoluble residue;
e. triturating the hexane insoluble residue as obtained in step (d) with chloroform to obtain chloroform soluble fraction and chloroform insoluble residue;
f. suspending the chloroform insoluble residue as obtained in step (e) with water followed by extracting with n-butanol to obtain n-butanol soluble fraction F004;
g. isolating the compounds 1 to 13 from fraction F004 by chromatographic methods.

In an embodiment of theinventio, wherein the alcohol used in step (b) may be selected from the group consisting of methanol, ethanol, propanol or suitable combination thereof.

In another embodiment of the invention, wherein the compounds 1 to 13 may be isolated from n-butanol soluble fraction F004 having the following formulae:

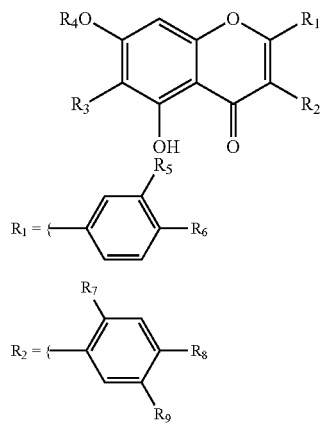

1: $R_1=R_3=R_4=H$, $R_2$: $R_7=R_9=H$, $R_8=OCH_3$
2: $R_1=H$, $R_3=OCH_3$, $R_4=Glc$, $R_2$: $R_7=R_8R_9=OCH_3$
3: $R_1=R_3=R_4=H$, $R_2$: $R_7=H$, $R_8=OH$, $R_9=OCH_3$
4: $R_1=R_3=R_4=H$, $R_2$: $R_7=R_9=H$, $R_8=OH$
5: $R_3=R_4=H$, $R_1$: $R_5=R_6=OH$, $R_2$: ORutinosyl
6: $R_1=R_3=H$, $R_4=Glc$, $R_2$: $R_7=R_9=H$, $R_8=OCH_3$
7: $R_3=R_4=H$, $R_1$: $R_5=H$, $R_6=OH$, $R_2$: ORutinosyl
8: $R_3=R_4=H$, $R_1$: $R_5=R_6=OH$, $R_2$: OGlc
9: $R_3=R_4=H$, $R_1$: $R_5=H$, $R_6=OH$, $R_2$: OGlc
10: $R_1=H$, $R_3=OCH_3$, $R_4=Apio(1\to6)$-Glc, $R_2$: $R_7=R_8=R_9=OCH_3$
11: $R_1=R_3=H$, $R_4=Apio(1\to6)$-Glc, $R_2$: $R_7=R_9=H$, $R_8=OCH_3$
12: $R_1=R_3=H$, $R_4=Apio(1\to5)$-Apio(1\to6)-Glc, $R_2$: $R_7=R_9=H$, $R_8=OCH_3$
13: $R_1=R_4=H$, $R_3=OCH_3$, $R_2$: $R_7=R_8=R_9=OCH_3$ In still another embodiment of the invention, wherein the alcoholic extract A001 obtained in step (c) comprising Compound 1 Biochanin A in the range of 1.0% to 3.0%,
Compound 2 (Caviunin 7-O-β-D-glycopyranoside)
Compound 3 Pratensein or 3'-methoxygenistein in the range of 0.1% to 0.5%,
Compound 4 Genstein in the range of 0.02% to 0.2%,
Compound 5 Quercetin 3-O-rutinoside in the range of 0.2% to 1.5%,
Compound 6 Biochanin 7-O-β-D-glucopyranoside in the range of 0.1% to 0.4%,
Compound 7 (Kampferol-3-O— rutinoside)
Compound 8 (Kaempferol 3-O-β-D-glucopyranoside)
Compound 9 (Quercetin 3-O-β-D-glucopyranoside)
Compound 10 Caviunin 7-O-[β-D-apiofuranosyl-(1→6)-β-D-glucopyranoside] in the range of 0.1% to 0.5%,
Compound 11 Biochanin A 7-O-[β-D-apiofuranosyl-(1→6)-β-D-glycopyranoside in the range of 0.5% to 2.0%
Compound 12 Biochanin A 7-O-[β-D-apiofuranosyl-(1→5)β-D-apiofuranosyl-(1→6)-β-D-glycopyranoside] in the range of 1.0% to 5.0%
Compound 13 (Caviunin)

In an embodiment of the invention wherein the compounds 1 to 13 may be isolated from the alcoholic extract A001 or fraction F004 by chromatographic methods selected from the group consisting of column chromatography, flash chromatography, medium pressure liquid chromatography, high performance liquid chromatography, gel filtration.

In a further embodiment of the invention wherein the compound 1, 2, 3, 4, and 6 are useful for the treatment of bone-joint disorder or osteo health related disorder.

In yet another embodiment of the invention wherein the compound 4 showed in vivo osteogenic activity in rats at a dose each 5.0 mg·kg$^{-1}$·day$^{-1}$ for 3 consecutive days and showed 5-fold increase in BMP-2 expression in primary calvarial osteoblast cells.

In still another embodiment of the invention wherein the compound is selected from a group consisting of 1, 3, 4, and 6 are non toxic to the cells at concentration ranging between 1 pM to 1 µM for 48 h.

One more embodiment of the invention, wherein the compound is selected from a group consisting of 1, 3, 4, and 6 showed proliferation of the osteoblastic cells at concentration ranging between 1 pM to 1 µM and do not cause cell growth arrest.

A pharmaceutical composition comprising compounds, selected from the group consisting of compounds 1, 3, 4, 6 or 10, in any combination optionally along with pharmaceutically acceptable carrier and additives.

In another embodiment of the present invention, wherein the combination of compounds 1, 3, 4, 6 and 10 in pharmaceutical composition may be in the ratio of 22.6:2:1:2:2.5 respectively In another embodiment of the present invention, wherein the combination of compounds 1, 3, 4 and 10 in pharmaceutical composition may be in the ratio of 1:6:11:54 respectively. In yet another embodiment of the present invention, the carrier used in pharmaceutical composition may be selected from the group consisting of gum acacia, carboxy methyl cellulose or any other known pharmaceutically acceptable carrier.

In yet another embodiment of the present invention, the pharmaceutical diluent used for the preparation of pharmaceutical may be selected from the group consisting of lactose, mannitol, sorbitol, microcrystalline cellulose, sucrose, sodium citrate, dicalcium phosphate, or any other ingredient of the similar nature alone or in a suitable combination thereof.

In still another embodiment of the present invention, the effective dose of the pharmaceutical composition is ranging between 0.1 to 5000 mg per kg body weight preferably 1 mg to 500 mg per kg body weight, daily, bi-weekly, weekly or in more divided doses.

In yet another embodiment of the present invention, the pharmaceutical composition is useful for the prevention or treatment of bone disorders may be any diseases and syndromes caused by osteoporosis, bone loss, bone formation, bone fracture healing, attainment of higher peak bone mass when administered during the period of growth, and promotion of new bone formation in vitro/in vivo.

In still another embodiment of the present invention, a method for prevention or treatment of bone disorders comprising the steps of administering a pharmaceutical composition to the subject in need optionally along with pharmaceutically acceptable excipients.

In yet another embodiment of the present invention, the pharmaceutical composition is administered by the route selected from oral, percutaneous, intramuscular, intraperitoneal, intravenous and local.

In still another embodiment of the present invention, the pharmaceutical composition may be used in a dose ranging between 1 to 5000 mg/kg body weight.

In yet another embodiment of the present invention, the pharmaceutical composition may be used in the form of tablet, syrup, powder, capsule, suspension, solution, ointment and mixture.

A pharmaceutical composition comprising compound 10, optionally along with pharmaceutically acceptable carrier, diluent and additives.

In an embodiment of the invention wherein the pharmaceutical composition comprising compound 10, optionally along with pharmaceutically acceptable carrier, diluent and additives for the prevention or treatment of bone-joint disorder or osteo-health related disorder.

A method for prevention or treatment of bone disorders wherein the said method comprising the steps of administering to the subject in need a pharmaceutical composition comprising compounds selected from the group consisting of 1, 3, 4, 6 or 10 optionally along with pharmaceutically acceptable carrier, diluent and additives.

ABBREVIATIONS

A001: Ethanolic extract of *Dalbergia sissoo* leaves
ALP: Alkaline Phosphatase
α-MEM: Alpha-minimum essential medium
Aβ: β-amyloid peptides
BFR: Bone formation rate
BMCs: Bone marrow cells
BV/TV: Bone Volume/Tissue Volume
cbfa1: Core Binding factor α 1
CDRI: Central Drug Research Institute
$CO_2$: Carbon di-oxide
CTX: Carboxyterminal telopeptide
CC: column chromatography
$CD_3OD$: deuterated methanol
$CDCl_3$: deuterated chloroform
$CHCl_3$ chloroform
COSY: correlation spectroscopy
d: doublet
dd: doublet of doublet
DMSO: Dimethyl Sulfoxide
DMSO-$d_6$: dutrated dimethyl sulphoxide
ESIMS: electrospray ionization mass spectrometry
ft: foot
E2: Estradiol
EST: Estradiol
F002: n-hexene fraction of ethanolic extract *Dalbergia sissoo* leaves
F003: Chloroform fraction of ethanolic extract *Dalbergia sissoo* leaves
F004: n-butanol fraction of ethanolic extract *Dalbergia sissoo* leaves
F005: Aqueous fraction of ethanolic extract *Dalbergia sissoo* leaves
FBS: Fetal Bovine Serum
g: gram
GH: Growth Hormone
H&E staining: Hemotoxin & Eosin staining
h.: hour
HPLC: High Performance Liquid Chromatography
HRT: Hormone Replacement Therapy
Hz: hertz
IAEC: Institutional Animal Ethical Committee
J: coupling constant
kg: kilogram
l: liter
m: multiplet
MAR: Mineral Apposition Rate
MeOH: methanol
MHz: megahertz
mg: milligram
min: minutes
mM: mill Molar
mm: millimeter
ml: milliliter
mp: melting point
m/z: mass number to charge ratio
n-BuOH: n-butanol
nM: nano Molar
NMR: nuclear magnetic resonance
s: singlet
TLC: thin layer chromatography
U.P.: Uttar Pradesh
μCT: Micro Computational Tomography
μL: Micro Litter
μm: Micro meters
μM: Micromolar
O.D.: Optical Density
OVx: Overiectomized
P: Probability
PB: Peak Bone Mass
PBS: Phosphate Buffer Salaine
pM: pico Molar
RNA: Ribo nucleic Acid
rpm: revolution per minute
S.D.: Standard Deviation
S.E.M.: Standard Error Mean
SMI: Structural Model Index
Tb. No.: Trabacular Numbers
Tb. Sp.: Trabacular separation
Tb. Th.: Trabacular thickness
TLC: Thin Layer Chromatography
U.P.: Uttar Pradesh
U/ml: Unit/milliliter
WHO: World Health Organization

BRIEF DESCRIPTION OF THE DRAWINGS

FIG. 5: Effect of A-4744/F004 extract on Bone histomorphometry

DESCRIPTION OF THE INVENTION

Figure 1:
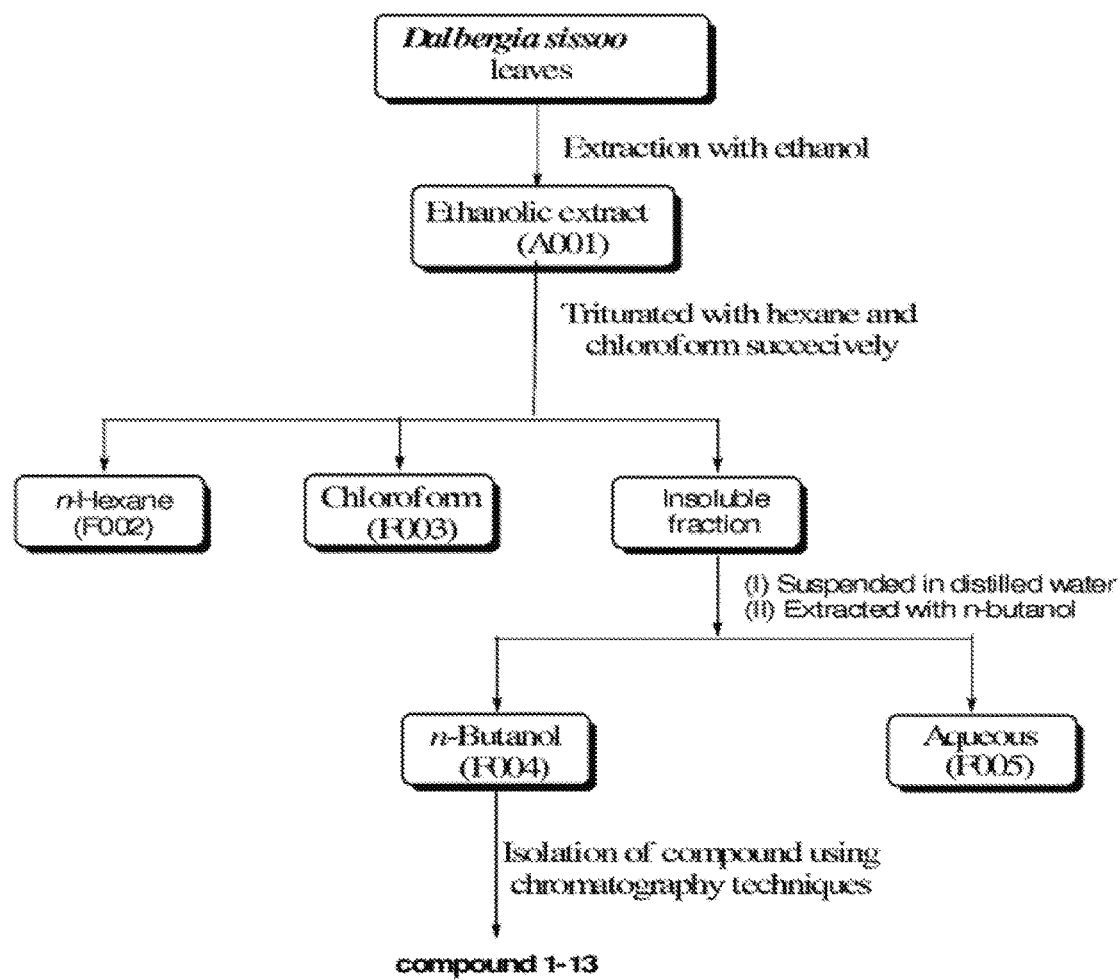
FIG. 1: Flow chart for preparation of compounds.

Accordingly, the present invention provides a process for the extraction and isolation and quantification of compounds of the formula I-13 shown in the drawing accompanying this specification, which comprises:

(a) providing plant component part (leaves) of the *Dalbergia sissoo;*
(b) powdering of the plant material,
(c) extracting the powdered plant material with protic solvent at room temperature,
(d) filtering the extract,
(e) concentrating the extract under reduced pressure,
(f) triturating the extract with hexane and chloroform to remove the nonpolar constituents,
(g) dissolving the extract in water,
(h) partitioning with n-butanol saturated with water,
(i) concentrating n-butanol soluble portion under vacuum to obtain free flowing powder to form the product with the desired composition designated as "osteoNATURALcare",
(j) isolating the compounds including but not limiting to 1-13 from the n-butanol soluble fraction by conventional chromatographic methods,
(k) quantifying the active compounds including but not limiting to 1, 3-5 and 10-12 in n-butanol soluble fraction or in any other fraction derived from *Dalbergia sissoo.*

Methods of preventing or treating disorders or disease conditions mentioned herein comprise administering to an individual human being or any other mammal or any other animal in need of such treatment a therapeutically effective amount of one or more of the agents of this invention.

The dosage regimen and the mode of administration of the agents of this invention or a pharmaceutically acceptable salt or a pharmaceutically acceptable composition thereof with one or more of the pharmaceutically acceptable carriers, excipients etc. will vary according to the type of disorder or disease conditions described herein and will be subject to the judgment of the medical practitioner involved.

The agent of this invention or a pharmaceutically acceptable salt or a pharmaceutically acceptable composition thereof with one or more of the pharmaceutically acceptable carriers, excipients etc. may be effectively administered in doses ranging from 0.1 mg to 5000 mg, more preferably in doses ranging from 0.5 to 1000 or still more preferably in the doses ranging from 1 mg to 500 mg weekly or bi-weekly or daily or twice a day or three times a day or in still more divided doses.

Such doses may be administered by any appropriate route for example, oral, systemic, local or topical delivery for example, intravenous, intra-arterial, intra-muscular, subcutaneous, intra-peritoneal, intra-dermal, buccal, intranasal, inhalation, vaginal, rectal, transdermal or any other suitable means in any conventional liquid or solid dosage form to achieve, conventional delivery, controlled delivery or targeted delivery of the compounds of this invention or a pharmaceutically acceptable salt or a pharmaceutically acceptable composition thereof with one or more of the pharmaceutically acceptable carriers, excipients etc.

A preferred mode of administration of agents of the present invention or a pharmaceutically acceptable salt or a pharmaceutically acceptable composition thereof is oral. Oral compositions will generally comprise of agents of the present invention or a pharmaceutically acceptable composition thereof and one or more of the pharmaceutically acceptable excipients.

The oral compositions such as tablets, pills, capsules, powders, granules, and the likes may contain any of the following pharmaceutically acceptable excipients:

1. a diluent such as lactose, mannitol, sorbitol, microcrystalline cellulose, sucrose, sodium citrate, dicalcium phosphate, or any other ingredient of the similar nature alone or in a suitable combination thereof;
2. a binder such as gum tragacanth, gum acacia, methyl cellulose, gelatin, polyvinyl pyrrolidone, starch or any other ingredient of the similar nature alone or in a suitable combination thereof;
3. a disintegrating agent such as agar-agar, calcium carbonate, sodium carbonate, silicates, alginic acid, corn starch, potato tapioca starch, primogel or any other ingredient of the similar nature alone or in a suitable combination thereof;
4. a lubricant such as magnesium stearate, calcium stearate or steorotes, talc, solid polyethylene glycols, sodium lauryl sulphate or any other ingredient of the similar nature alone or in a suitable combination thereof;
5. a glidant such as colloidal silicon dioxide or any other ingredient of the similar nature alone or in a suitable combination thereof;
6. a sweetening agent such as sucrose, saccharin or any other ingredient of the similar nature alone or in a suitable combination thereof;
7. a flavoring agent such as peppermint, methyl salicylate, orange flavor, vanilla flavor, or any other pharmaceutically acceptable flavor alone or in a suitable combination thereof;
8. wetting agents such as cetyl alcohol, glyceryl monostearate or any other pharmaceutically acceptable flavor alone or in a suitable combination thereof;
9. absorbents such as kaolin, bentonite clay or any other pharmaceutically acceptable flavor alone or in a suitable combination thereof;
10. solution retarding agents such as wax, paraffin or any other pharmaceutically acceptable flavor alone or in a suitable combination thereof.

Therefore, the present invention seeks to overcome prior problems associated with the cure and the management associated with estrogen dependent or independent diseases or syndromes or disorders preferably in the prevention or treatment of estrogen dependent or independent diseases caused in humans and animals and more particularly the bone health disorders and syndromes. The invention also seeks to promote peak bone mass achievement during skeletal growth as occurs in adolescence. The n-butanol soluble fraction and the pure compounds 1-13 from *Dalbergia sissoo* described in the present invention are useful in the management, prevention treatment, and cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

Accordingly the present invention provides a crude extract or n-butanol soluble fraction or individual pure compounds or cocktail of suitable ratio or ratios of two or more than two pure compounds derived from *Dalbergia sissoo* in pharmaceutically acceptable form to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals, by the process and the methods described in the present invention.

The invention discloses the crude extract useful for management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals, is prepared from the leaves of the plant *Dalbergia sissoo*.

The invention also discloses the n-butanol soluble fraction, useful for management or prevention or treatment or cure of estrogen dependent or independent diseases or syndromes or disorders preferably in the prevention or treatment of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals, is prepared from the crude extract of the leaves of the plant *Dalbergia sissoo*.

The invention discusses the individual pure compounds, useful for management or prevention or treatment or cure of estrogen dependent or independent diseases or syndromes or disorders preferably in the prevention or treatment of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals, are derived from the crude extract or n-butanol soluble fraction of the leaves of the plant *Dalbergia sissoo*.

The invention shows the ratios and absolute concentration of the individual pure compounds in the crude extract or n-butanol soluble fraction of *Dalbergia sissoo* and useful for management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

The invention exhibits the individual pure compounds in the crude extract or n-butanol soluble fraction of *Dalbergia sissoo* were evaluated in-vitro and vivo using well established protocols and procedures to establish and demonstrate their usefulness in management or prevention or treatment or cure of estrogen dependent or independent diseases or syndromes or disorders preferably in the prevention or treatment of estrogen dependent or independent diseases or syndromes or disorders caused in humans and animals, and achievement of PBM during skeletal growth and health in humans and animals.

The invention is described by way of illustrative examples and should not be construed to limit the scope of the invention to the accompanying formula drawings.

EXAMPLES

Following examples are given by way of illustration of the invention and should not be construed to limit the scope of the present invention 1. Extraction with Ethanol of *Dalbergia sissoo* Leaves

*Dalbergia sissoo* Roxb. belongs to the family Fabaceae, is distributed throughout sub-Himalayan tract from Ravi to Assam ascending up to 5000 ft in India, Pakistan, Bangladesh and Afghanistan. *Dalbergia sissoo*, commonly known as "Shisham" in India, *Dalbergia sissoo* was collected from Lucknow, U. P. India. Lucknow is located at 26° 48' North and 80° 54' East. Powdered leaves of *Dalbergia sissoo* (Plant code No. 4744, 18 kg) were placed in glass percolator with ethanol (40 L) and are allowed to stand at room temperature for about 16 hours (overnight). The percolate was collected. This process of extraction was repeated for five times. The combined extract was filtered, concentrated at 45° C.; weight of extract obtained 2.00 kg (11.1%, 4744-A001).

2. Fractionation

Ethanolic extract (4744-A001, 1.80 kg) was triturated with hexane (1000 ml×8). The hexane soluble fraction was then concentrated under the reduced pressure at 40° C., weight of hexane fraction obtained 427.0 g (23.7%, F002). Residue obtained after triturating with hexane was again triturated with chloroform (1000 ml×8). The chloroform soluble fraction was then concentrated under the reduced pressure at 40° C., weight of chloroform fraction obtained 333.0 g (18.5%, F003). The insoluble residue was suspended in water (2500 ml), extracted with n-butanol saturated with water ((1500 ml×7) ml). The combined n-butanol soluble fraction was concentrated under the reduced pressure at 45° C., weight of n-butanol soluble fraction δ40.0 g (41.1%, F004).

3. Isolation of Compounds from n-Butanol Soluble Fraction (F004) of *Dalbergia sissoo*

The n-BuOH fraction (600.0 g) was subjected to silica gel column chromatography (100-200 mesh), with the gradient of $CHCl_3$-MeOH (90:10, 90:20, 70:30, 50:40, 50:50 and MeOH) as eluent. Six fractions (F1-F6) were collected according to TLC analysis. Fraction F1 was purified on silica gel column chromatography eluted with pure $CHCl_3$ afforded 13 and $CHCl_3$-MeOH (95:5) to afforded compounds 1, 4 and compound 3 successively. Purification of F2 fraction by repeated column chromatography on silica gel eluted with $CHCl_3$-MeOH (90:10 to 85:15) to afforded compounds 2 and 6. Purification of F3 fraction on silica gel followed by CC over Sephadex-LH25 and C18 column chromatography eluted with MeOH—$H_2O$ (30:70) afforded compounds 9, 7 compound 10 and compound 11. Fraction F4 afforded compound 12, compound 8 and compound 5 by CC over Sephadex-LH-25 eluted with MeOH—$H_2O$ (30:

70), followed by repeated C18 CC eluted with MeOH—H$_2$O. The flow chart for the isolation procedure is provided in FIG. 1. Accordingly butanol fraction afforded 13 compounds designated as 1-13. These compounds were characterized from detailed spectroscopic studies. The compound 10 is new reported for the first time from natural source. We have given the common name to 10 (Dalsissooside). The compounds 1-9 and 11-13 are known.

Physical and spectral data of isolated compounds

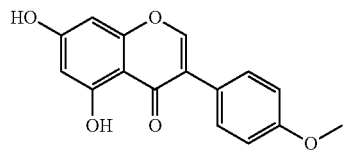

1

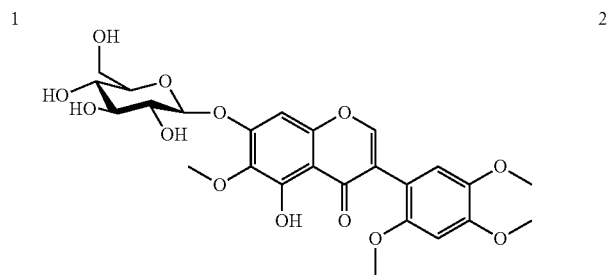

2

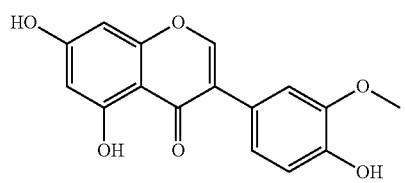

3

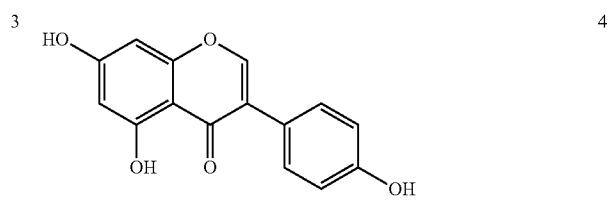

4

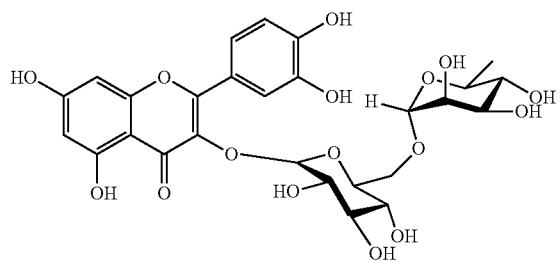

5

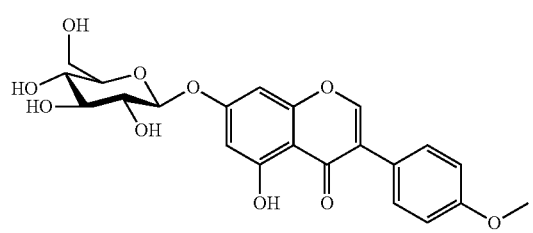

6

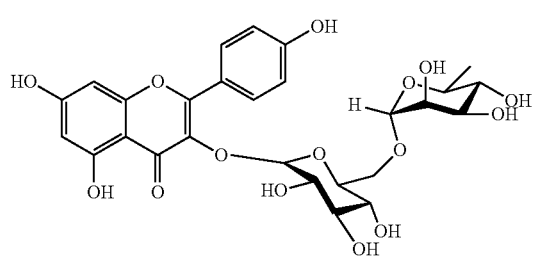

7

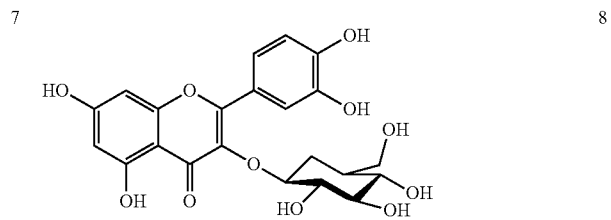

8

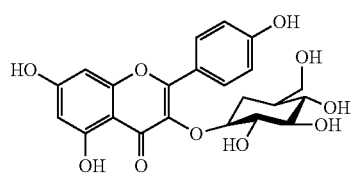

9

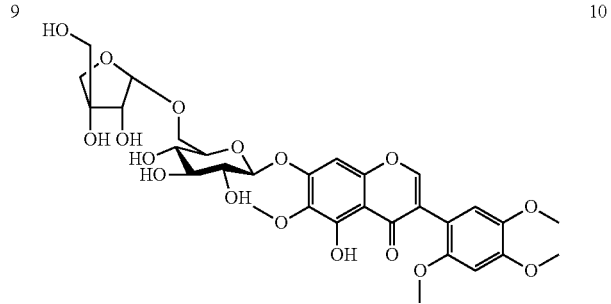

10

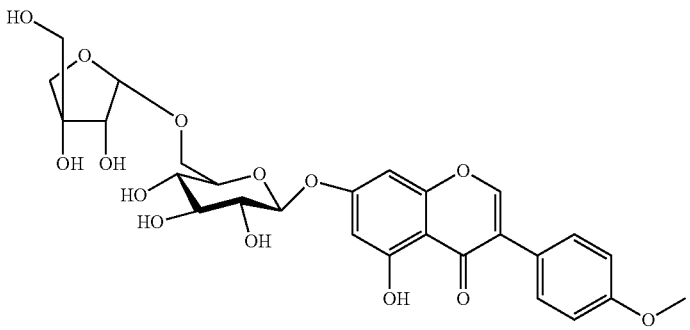

11

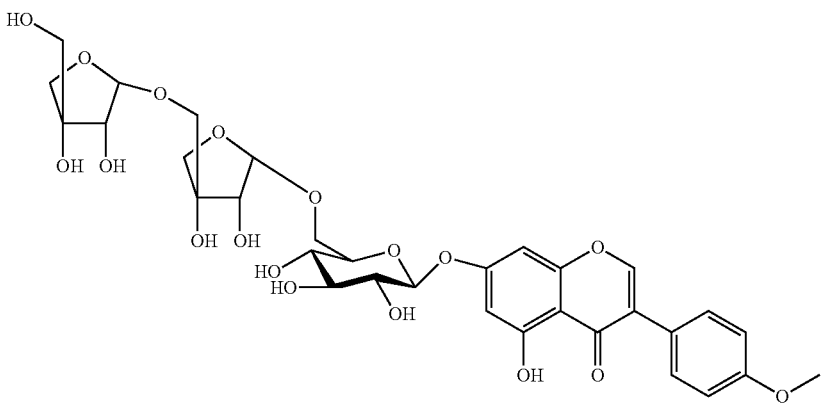

12

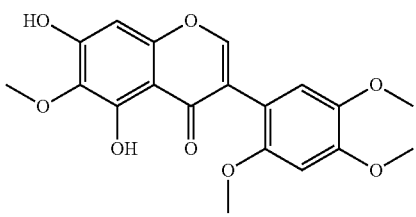

13

4. Characterization of Isolated Compounds 1-13

Compound 1 (Biochanin A)

Yield: 7.8 g. (1.3%); light yellow needle shape crystals; mp: 214-216° C.; ESIMS: m/z 285[M+1]$^+$; $C_{16}H_{12}O_5$; $^1$H NMR: (DMSO-$d_6$, 300 MHz) δ: 8.22 (1H, s, H-2), 6.22 (1H, d, J=2.0 Hz, H-6), 6.34 (1H, d, J=2.0 Hz, H-8), 7.45 (2H, d, J=8.7 Hz, H-2', 6'), 6.95 (2H, d, J=8.7 Hz, H-3', 5'), 12.89 (1H, s, OH-5), 3.79 (3H, s, 4'-OCH$_3$); $^{13}$C NMR: (DMSO-$d_6$, 75 MHz) δ: 153.6 (C-2), 121.6 (C-3), 179.7 (C-4), 161.7 (C-5), 98.7 (C-6), 163.9 (C-7), 93.4 (C-8), 157.2 (C-9), 104.1 (C-10), 122.6 (C-1'), 129.8 (C-2',6'), 113.3 (C-3',5'), 158.8 (C-4'), 55.1 (3H, s, 4'-OCH$_3$).

Compound 2 (Caviunin 7-O-β-D-glycopyranoside)

Yield: 2 g. (0.33%); light yellow coloured needle shape crystals; mp: 235-236° C.; ESIMS: m/z 559 [M+Na+1]$^+$, 537 [M+1]$^+$; $C_{25}H_{28}O_{13}$, $^1$H NMR: (DMSO-$d_6$, 300 MHz) δ 8.29 (1H, s, H-2), 6.88 (1H, s, H-8), 6.78 (1H, s, H-3'), 6.90 (1H, s, H-6'), 5.07 (1H, d, J=4.83 Hz, H-1"), and other sugar protons are at 3.60-3.10 (5H, m, H-2"-6"), 12.87 (1H, s, OH-5), 5.45 (1H, s, OH-2") 5.14 (2H, s, OH-3",4") 4.63 (1H, m, OH-6"), 3.77 (3H, s, 6-OCH$_3$) 3.72 (3H, s, 2'-OCH$_3$) 3.83 (3H, s, 4'-OCH$_3$) 3.70 (3H, s, 5'-OCH$_3$). $^{13}$C NMR: (DMSO-$d_6$, 75 MHz) δ: 156.1 (C-2), 120.0 (C-3), 180.6 (C-4), 152.8 (C-5), 132.6 (C-6), 156.6 (C-7), 94.2 (C-8), 152.1 (C-9), 106.4 (C-10), 110.5 (C-1'), 152.5 (C-2'), 98.6 (C-3'), 150.0 (C-4'), 142.4 (C-5'), 116.1 (C-6'), 100.2 (0-1"), 73.2 (C-2"), 76.7 (C-3"), 69.7 (C-4"), 77.3 (C-5"), 60.4 (C-6"), 60.0 (6-OCH$_3$), 56.5 (2'-OCH$_3$), 55.9 (4'-OCH$_3$), 56.5 (5'-OCH$_3$).

Compound 3 (Pratensein or 3'-methoxygenistein)

Yield: 300 mg. (0.05%); light yellow crystals; mp: 273-274° C.; ESIMS: m/z 301[M+1]$^+$; $C_{16}H_{12}O_6$; $^1$H NMR: (DMSO-$d_6$, 300 MHz) δ: 8.30 (1, s, H-2), 6.22 (1H, dd, J=1.9 Hz, H-6), 6.38 (1H, d, J=2 Hz, H-8), 6.95 (2H, s, H-2',6'), 7.03 (1H, s, H-5'), 3.79 (3'-OCH$_3$); $^{13}$C NMR: (DMSO-$d_6$, 75 MHz) δ: 154.3 (C-2), 123.4 (C-3), 180.3 (C-4), 162.1 (C-5), 99.1 (C-6), 164.4 (C-7), 93.8 (C-8), 157.6 (C-9), 104.6 (C-10), 122.2 (C-1'), 112.0 (C-2'), 147.8 (C-3'), 146.2 (C-4'), 116.5 (C-5'), 119.9 (C-6'), 55.7 (3'-OCH$_3$).

Compound 4 (Genstein)

Yield: 0.5 g. (0.083%); light yellow crystals; mp: 299-302° C.; ESIMS: m/z 271[M+1]$^+$; $C_{15}H_{10}O_5$; $^1$H NMR: (CD$_3$OD, 300 MHz) δ: 8.01 (1H, s, H-2), 6.21 (1H, d, J=2.0

Hz, H-6), 6.32 (1H, d, J=2.0 Hz, H-8), 7.35 (2H, d, J=8.5 Hz, H-2',6'), 6.85 (2H, d, J=8.5 Hz, H-3', 5'); $^{13}$C NMR: (CD$_3$OD, 75 MHz) δ: 154.9 (C-2), 124.8 (C-3), 182.4 (C-4), 163.9 (C-5), 100.3 (C-6), 166.0 (C-7), 94.9 (C-8), 158.9 (C-9), 106.4 (C-10), 123.4 (C-1'), 131.6 (0-2',6'), 116.5 (C-3',5'), 159.8 (C-4').

Compound 5 (Quercetin 3-O-rutinoside)

Yield: 2.0 g. (0.33%); yellow crystalline solid; mp: 213-215° C.; ESIMS: m/z 633[M+Na]$^+$; C$_{27}$H$_{30}$O$_{16}$; $^1$H NMR: (Pyridine-d$_5$, 300 MHz) δ 6.71 (1H, d, J=1.2 Hz, H-6), 6.67 (1H, d, J=1.2 Hz, H-8), 8.41 (1H, d, J=2.0 Hz H-2'), 7.28 (1H, d, J=8.2 Hz H-5'), 8.14 (1H, dd, J=8.2, 2.0 Hz, H-6'), 5.95 (1H, d, J=7.7 Hz, H-1") 5.28 (1H, s, H-1''') and other sugar protons are at 4.80-4.02 (10H, m, H-2"-6" and 2'''-5'''), 1.53 (3H, d, J=5.5 Hz, H-6'''), 13.12 (1H, s, OH-5); $^{13}$C NMR: (DMSO-d$_6$, 75 MHz) δ: 158.6 (C-2), 135.5 (C-3), 179.2 (C-4), 163.1 (C-5), 100.3 (C-6), 166.5 (C-7), 95.1 (C-8), 158.1 (C-9), 105.6 (C-10), 122.8 (C-1'), 118.4 (C-2'), 147.4 (C-3'), 151.5 (C-4'), 116.7 (C-5'), 123.4 (C-6'), 106.2 (C-1"), 74.4 (C-2"), 75.8 (C-3"), 70.2 (C-4"), 75.8 (C-5"), 67.6 (C-6"), 102.6 (0-1'''), 72.7 (C-2'''), 73.2 (C-3'''), 73.8 (C-4'''), 70.2 (C-5'''), 19.1 (C-6''').

Compound 6 (Biochanin 7-O-glycoside)

Yield: 0.753 g. (0.125%); light yellow crystals; mp: 206-208° C.; ESIMS: m/z 447 [M+1]$^+$; C$_{22}$H$_{22}$O$_{10}$; $^1$H NMR: (DMSO-d$_6$, 300 MHz) δ: 8.44 (1H, s, H-2), 6.48 (1H, s, H-6), 6.72 (1H, s, H-8), 7.53 (2H, d, J=6.4 Hz, H-2', 6'), 7.01 (2H, d, J=6.4 Hz, H-3', 5'), 5.07 (1H, d, J=4.83 Hz, H-1"), and other sugar protons are at 3.79-3.19 (5H, m, H-2"-6"), 12.89 (1H, s, OH-5), 5.43 (1H, s, OH-2") 5.13 (2H, s, OH-3",4") 4.62 (1H, m, OH-6"), 3.79 (3H, s, 4'-OCH$_3$); $^{13}$C NMR: (DMSO-d$_6$, 75 MHz) δ: 153.6 (C-2), 123.2 (C-3), 180.9 (C-4), 162.1 (C-5), 100.1 (C-6), 163.5 (C-7), 95.0 (C-8), 157.7 (C-9), 106.5 (C-10), 122.7 (C-1'), 130.6 (C-2',6'), 114.2 (C-3',5'), 159.7 (C-4'), 100.3 (C-1"), 73.5 (C-2"), 76.8 (C-3"), 70.0 (C-4"), 77.5 (C-5"), 61.1 (C-6"), 55.6 (3H, s, 4'-OCH$_3$).

Compound 7 (Kampferol-3-O-rutinoside)

Yield: 0.70 g. (0.117%); yellowish needle shape crystals; m.p. 186-188° C.; ESIMS: m/z 617 [M+Na]$^+$; C$_{27}$H$_{30}$O$_{15}$; $^1$H NMR: (CD$_3$OD, 300 MHz) δ 6.17 (1H, d, J=2.0 Hz H-6), 6.37 (1H, d, J=2.0 Hz H-8), 8.08 (1H, d, J=8.7 Hz, H-2', 6'), 6.88 (1H, d, J=8.7 Hz, H-3', 5'), 5.03 (1H, d, J=7.9 Hz, H-1") 4.52 (1H, s, H-1''') and other sugar protons are at 4.21-3.02 (10H, m, H-2"-6" and 2'''-5''', merged with methanol), 1.26 (3H, d, H-6'''); $^{13}$C NMR: (CD$_3$OD-d$_6$, 75 MHz) δ: 160.4 (C-2), 133.7 (C-3), 177.9 (C-4), 161.6 (C-5), 98.9 (C-6), 164.9 (C-7), 93.7 (C-8), 157.4 (C-9), 103.4 (C-10), 121.3 (C-1'), 131.4 (C-2', 6'), 115.5 (C-3', 5'), 160.4 (C-4'), 102.5 (C-1"), 73.23 (C-2"), 74.0 (C-3"), 68.7 (C-4"), 73.5 (C-5"), 65.8 (C-6"), 100.5 (C-1'''), 70.9 (C-2'''), 71.6 (C-3'''), 72.4 (C-4'''), 68.5 (0-5"), 18.3 (0-6").

Compound 8 (Kaempferol 3-O-β-D-glucopyranoside)

Yield: 0.055 g. (0.009%); yellow amorphous solid; ESIMS: m/z 449 [M+H]$^+$; C$_{21}$H$_{20}$O$_{11}$; $^1$H NMR: (CD$_3$OD, 300 MHz) δ 6.19 (1H, s, H-6), 6.39 (1H, s, H-8), 8.04 (1H, d, J=8.7 Hz, H-2', 6'), 6.88 (1H, d, J=8.7 Hz, H-3', 5'), 5.24 (1H, d, J=7.9 Hz, H-1") and other sugar protons are at 3.87-3.10 (5H, m, H-2"-6", merged with methanol); $^{13}$C NMR: (DMSO-d$_6$, 75 MHz) δ: 161.6 (C-2), 135.6 (C-3), 179.6 (C-4), 161.6 (C-5), 99.9 (C-6), 166.0 (C-7), 94.9 (C-8), 158.5 (C-9), 104.2 (C-10), 122.9 (C-1'), 132.4 (C-2', 6'), 116.2 (C-3', 5'), 161.6 (C-4'), 100.0 (C-1"), 75.8 (C-2"), 78.5 (C-3"), 71.4 (C-4"), 79.2 (C-5"), 62.7 (C-6").

Compound 9 (Quercetin 3-O-β-D-glucopyranoside)

Yield: 0.05 g. (0.008%); yellowish white powder; ESIMS: m/z 465 [M+H]$^+$; C$_{21}$H$_{20}$O$_{12}$; $^1$H NMR: (DMSO-d$_6$, 300 MHz) δ 6.21 (1H, d, J=1.6, H-6), 6.42 (1H, d, J=1.6, H-8), 7.60 (1H, m, H-2'), 6.86 (1H, d, J=8.7 Hz, H-5'), 7.60 (1H. m, 6'), 5.45 (1H, d, J=7.9 Hz, H-1") and other sugar protons are at 3.77-3.11 (5H, m, H-2"-6"); $^{13}$C NMR: (DMSO-d$_6$, 75 MHz) δ: 156.6 (C-2), 133.6 (C-3), 177.7 (C-4), 161.4 (C-5), 99.0 (C-6), 164.4 (C-7), 93.8 (C-8), 156.5 (C-9), 104.2 (C-10), 121.9 (C-1'), 115.5 (C-2'), 145.0 (C-3'), 148.7 (C-4'), 116.5 (C-5'), 121.4 (C-6'), 101.2 (C-1"), 75.9 (C-2"), 76.7 (C-3"), 70.1 (C-4"), 77.7 (C-5"), 61.2 (C-6").

Compound 10 (Caviunin 7-O-[β-D-apiofuranosyl-(1→6)-β-D-glucopyranoside)

Yield: 0.20 g. (0.033%); brown fine crystals; m.p. 135-138° C.; ESIMS: m/z 669 [M+1]$^+$; C$_{30}$H$_{36}$O$_{17}$; $^1$H NMR: (DMSO-d$_6$, 300 MHz) δ 8.21 (1H, s, H-2), 6.90 (1H, s, H-8), 6.76 (1H, s, H-3'), 6.90 (1H, s, H-6'), 5.06 (1H, d, J=4.83 Hz, H-1"), 4.85 (1H, d, J=4.83 Hz, H-1'''), and other sugar protons are at 3.97-3.19 (11H, m, H-2"-6" and H-2'''-5'''), 12.88 (1H, s, OH-5), 5. 54, 5.27, 5.06 and 4.54 (6H, s, OH-2", 3", 4", 2''', 3''', and 5'''), 3.79 (3H, s, 6-OCH$_3$) 3.72 (3H, s, 2'-OCH$_3$) 3.83 (3H, s, 4'-OCH$_3$) 3.72 (3H, s, 5'-OCH$_3$). $^{13}$C NMR: (DMSO-d$_6$, 75 MHz) δ: 156.3 (C-2), 120.2 (C-3), 180.8 (C-4), 153.0 (C-5), 132.8 (C-6), 156.7 (C-7), 94.7 (C-8), 152.3 (C-9), 106.8 (C-10), 110.7 (C-1'), 152.8 (C-2'), 98.7 (C-3'), 150.3 (C-4'), 142.7 (C-5'), 116.2 (C-6'), 100.6 (C-1"), 73.6 (C-2"), 78.9 (C-3"), 70.2 (C-4"), 76.3 (C-5"), 68.1 (C-6"), 109.7 (C-1'''), 76.9 (C-2'''), 79.3 (C-3'''), 75.9 (C-4'''), 63.5 (C-5'''), 60.6 (6-OCH$_3$), 56.6 (2'-OCH$_3$), 56.1 (4'-OCH$_3$), 56.6 (5'-OCH$_3$).

Compound 11 (Biochanin A 7-O-[β-D-apiofuranosyl-(1→6)-β-D-glycopyranoside)

Yield: 0.05 g. (0.008%); light yellow crystals; m.p. 168-170° C.; ESIMS: m/z 579[M+1]$^+$; C$_{27}$H$_{30}$O$_{14}$; $^1$H NMR: (DMSO-d$_6$, 300 MHz) δ: 8.09 (1H, s, H-2), 6.45 (1H, s, H-6), 6.65 (1H, s, H-8), 7.45 (2H, d, J=7.7 Hz, H-2', 6'), 6.94 (2H, d, J=7.8 Hz, H-3', 5'), 4.91 (1H, d, J=7.4 Hz, H-1"), 4.98 (1H, d, J=2.4 Hz, H-11, and other sugar protons are at 4.05-3.35 (11H, m, H-2"-6" and H-2"-5"), 3.80 (3H, s, 4'-OCH$_3$); $^{13}$C NMR: (DMSO-d$_6$, 75 MHz) δ: 155.7 (C-2), 124.5 (C-3), 182.4 (C-4), 163.5 (C-5), 101.3 (C-6), 164.7 (C-7), 96.2 (C-8), 159.1 (C-9), 108.1 (C-10), 124.5 (C-1'), 131.4 (C-2',6'), 115.0 (C-3',5'), 161.3 (C-4'), 101.7 (C-1"), 74.7 (C-2"), 78.3 (C-3"), 71.7 (C-4"), 77.3 (C-5"), 69.2 (C-6"), 111.3 (C-1'''), 77.9 (C-2'''), 80.0 (C-3'''), 75.2 (C-4'''), 65.9 (C-5'''), 55.9 (3H, s, 4'-OCH$_3$).

Compound 12 (Biochanin A 7-O-[β-D-apiofuranosyl-(1→5)β-D-apiofuranosyl-(1→6)-β-D-glycopyranoside)

Yield: 1.0 g. (0.166%); yellow needle shape crystals; ESIMS: m/z 733[M+Na]$^+$; C$_{32}$H$_{38}$O$_{18}$, $^1$H NMR: (CD$_3$OD, 300 MHz) δ: 8.08 (1H, s, H-2), 6.45 (1H, s, H-6), 6.61 (1H, s, H-8), 7.45 (2H, d, J=7.7 Hz, H-2', 6'), 6.94 (2H, d, J=7.8 Hz, H-3', 5'), 4.91 (1H, d, J=7.4 Hz, H-1''), 4.98 (1H, d, J=2.4 Hz, H-1'''), 4.97 (1H, d, J=2.4 Hz, H-1'''') and other sugar protons are at 4.05-3.35 (16H, m, H-2''-6'' H-2'''-5''' and H-2''''-5'''' merged with methanol), 3.80 (3H, s, 4'-OCH$_3$); $^{13}$C NMR: (CD$_3$OD-d$_6$, 75 MHz) δ: 155.7 (C-2), 124.5 (C-3), 182.3 (C-4), 163.4 (C-5), 101.3 (C-6), 164.6 (C-7), 96.2 (C-8), 159.0 (C-9), 108.1 (C-10), 124.5 (C-1'), 131.4 (C-2',6'), 115.0 (C-3',5'), 161.3 (C-4'), 101.6 (C-1''), 74.7 (C-2''), 78.0 (C-3''), 71.9 (C-4''), 77.1 (C-5''), 69.1 (C-6''), 111.0 (C-1'''), 78.7 (C-2'''), 79.5 (C-3'''), 75.3 (C-4'''), 71.6 (C-5'''), 110.9 (C-1''''), 77.1 (C-2''''), 80.6 (C-3''''), 75.2 (C-4''''), 65.6 (C-5''''), 55.9 (3H, s, 4'-OCH$_3$).

Compound 13 (Caviunin)

Yield: 1.0 g. (0.166%); light yellow neddle; m.p. 192-193° C.; ESIMS: m/z 374 [M+1]$^+$; C$_{19}$H$_{18}$O$_8$; $^1$H NMR: (DMSO-d$_6$, 300 MHz) δ 8.20 (1H, s, H-2), 6.88 (1H, s, H-8), 6.78 (1H, s, H-3'), 6.56 (1H, s, H-6'), 13.01 (1H, s, OH-5), 10.8 (1H, s, OH-7'). $^{13}$C NMR: (DMSO-d$_6$, 75 MHz) δ: 155.5 (C-2), 119.6 (C-3), 180.6 (C-4), 152.8 (C-5), 131.4 (C-6), 157.4 (C-7), 93.9 (C-8), 153.1 (C-9), 104.8 (C-10), 110.7 (C-1'), 152.0 (C-2'), 98.6 (C-3'), 150.0 (C-4'), 142.4 (C-5'), 116.1 (C-6'), 59.9 (6-OCH$_3$), 56.5 (2'-OCH$_3$), 55.9 (4'-OCH$_3$), 56.5 (5'-OCH$_3$).

5. Quantification of Active Principles in Alcoholic Extract (A001) and n-Butanol Soluble Fraction (F004) Designated as osteoNATURALcare The mother stock solution of the extracts was prepared by dissolving 2 mg of each dried extract (F004 and A001) in 50 µL dimethyl sulfoxide and volume than made up to 1 mL using methanol to get a solution of 2 mg/mL.

The mother stock solutions of the active principles, namely 1, 3-5 and 10-12, were prepared by dissolving 1 mg of each compound in 50 µL DMSO and than volume made up to 1 mL using methanol to give a solutions of 1.0 mg/mL. Working standard solutions of all analytes were prepared by combining the aliquots of each mother stock solution and diluting with methanol.

The samples were analyzed by injecting 50 µL of each sample on HPLC. The separation was achieved on C18 column using 0.2% acetic acid (A) and acetonitrile (B) as a mobile phase at a flow rate of 1 ml per minute.

The concentration of components 1, 3-5 and 10-12 in n-butanol fraction (F004) and aqueous extract (A001) is given in following table-1

TABLE 1

Contents (mg/g) of investigated compounds in *Dalbergia* extract

| | | F004 | | A001 | |
|---|---|---|---|---|---|
| S.N. | Compounds | Mean ± S.D (mg/g) | % content | Mean ± S.D (mg/g) | % content |
| 1 | 1 | 7.72 ± 0.04 | 0.78 | 22.603 ± 0.89 | 2.26 |
| 2 | 3 | 3.92 ± 0.48 | 0.39 | 2.17 ± 0.13 | 0.22 |
| 3 | 4 | 0.70 ± 0.152 | 0.07 | 1.01 ± 0.37 | 0.10 |
| 4 | 5 | 24.67 ± 1.03 | 2.47 | 7.68 ± 0.13 | 0.77 |
| 5 | 6 | 4.00 ± 0.50 | 0.40 | 2.13 ± 0.12 | 0.20 |
| 6 | 10 | 37.59 ± 5.97 | 3.76 | 2.41 ± 0.14 | 0.24 |
| 7 | 11 | 42.87 ± 1.09 | 4.3 | 10.82 ± 0.76 | 1.08 |
| 8 | 12 | 194.45 ± 5.76 | 19.44 | 37.59 ± 4.08 | 3.76 |

6. Biological Evaluation

The plant extracts and isolated pure compounds thereof were evaluated for the use of estrogen dependent or independent diseases or syndromes or diseases preferably in the prevention or treatment of estrogen dependent or independent diseases or syndromes or diseases caused in humans and animals, and achievement of PBM during skeletal growth and health in mammals. The activity testing illustrated in the following examples should, however, not be construed to limit the scope of invention.

Treatment of n-Butanol Fraction (A-4744/F004) of *Dalbergia sissoo* in Ovariectomized Sprague Dawley Rats The study was conducted in accordance with current legislation on animal experiments [Institutional Animal Ethical Committee (IAEC)] at C.D.R.I. Immature Sprague Dawley rats weighing ~180-200 gm were either bilaterally ovariectomized (OVx) or exposed to a sham surgical procedure. All rats were individually housed at 21° C., in 12-h light:12-h dark cycles. All rats had excess to normal chow diet and water ad libitum. After OVx, the rats were left for 12 weeks to develop osteopenia. After 12 weeks, extract treatment in the form of gavage (50.0 mg and 100 mg/kg body weight) and estradiol (EST) at a dose of 2.5 mg/kg bodyweight) was given daily. Equal numbers of OVx and sham operated rats served as the control, and were given vehicle (20% ethanol). The rats were weighed each week. At the end of 12 weeks, urine was to be collected for biochemical assessment therefore the rats were caged individually in plastic cages fitted with steel mesh for a total period of 48 h preceding autopsy and had free access to normal chow diet and water for the first 24 h initially for of acclimatization and then during the next 24 h, animals received only water ad libitum. After twenty-four hours of fasting urine samples were collected in fresh containers, centrifuged at 2000 rpm at room temperature and stored at −20° C. until analyzed. Rats were then euthanized. At autopsy, blood samples were collected by cardiac puncture in tubes, and serum samples collected and frozen until analysis. Uteri were carefully excised, gently blotted, weighed, and fixed for histology and histomorphometry. About 5 mm pieces from the middle segment of each uterus were dehydrated in ascending grades of ethanol, cleared in xylene, and embedded in paraffin wax using standard procedures. Representative transverse sections (5 µm) were stained with H&E stain. Photomicrographs of sections were obtained using a Leica DC 300 camera and Leica IM50 Image Acquisition software fitted to a Leica DMLB microscope. Histomorphometric measurements were done using Leica Qwin-Semiautomatic image Analysis software. µCT (both 2-D and 3-D) determination of excised bones was carried out using the Sky Scan 1076 µCT scanner (Aartselaar, Belgium) using the cone-beam reconstruction software version 2.6 based on the Feldkamp algorithm (Skyscan). The bone marrow was harvested for ex vivo experiments. Both femora were dissected and separated from adjacent tissue, cleaned, and used for RNA isolation and also micro measurements.

Evaluation of Trabecular Microarchitecture

Trabecular response to A-4744/F004 treatment of OVx rats was quantified at the femur epiphysis and tibial proximal metaphysis. Femoral data show (table below) that compared with the sham group, the OVx+vehicle group had reduced BV/TV, Tb.No and Tb.Th, and increased Tb.sp and SMI. Comparison of the A-4744/F004 treatment group with the OVx+vehicle group revealed significant increase in BV/TV and Tb.Th., and decrease in Tb.sp and SMI, suggesting that the microarchitectural features of the femoral trabecular bones are significantly protected by A-4744/F004 treatment of OVx rats.

Ex-Vivo Culture of Bone Marrow Cells (BMCs)

Bone marrow cells (BMCs) from female Sprague Dawley rats weighing ~100-180 were isolated at the end of the

TABLE 2

μCT data of femur after 12 weeks of treatment of OVx rats with A-4744/F004

| Trabecular Parameters (Femur | SHAM | OVX | 50 mg · kg$^{-1}$ · day$^{-1}$ | 100 mg · kg$^{-1}$ · day$^{-1}$ | ESTRADIOL (E2) 2.5 μg · kg$^{-1}$ · day$^{-1}$ |
|---|---|---|---|---|---|
| BV/TV (%) | 64.07 ± 1.18*** | 52.98 ± 1.30 | 57.30 ± 0.68** | 57.46 ± 0.94** | 59.23 ± 30.19*** |
| Tb. Th. | 0.87 ± 0.02*** | 0.75 ± 0.01 | 0.83 ± 0.02** | 0.88 ± 0.005*** $^a$ | 0.78 ± 0.01 |
| Tb. Sp. | 0.50 ± 0.02*** | 1.12 ± 0.03 | 0.92 ± 0.08*** | 0.87 ± 0.041*** | 0.86 ± 0.004*** |
| Tb. No. | 0.721 ± 0.038 | 0.661 ± 0.023 | 0.641 ± 0.020 | 0.673 ± 0.024 | 0.725 ± 0.024 |
| SMI | 1.51 ± 0.14*** | 2.84 ± 0.17 | 2.13 ± 0.20** | 1.59 ± 0.12*** $^a$ | 2.41 ± 0.13 |

Values expressed as mean ± S.D. BV/TV, bone volume fraction; Tb. Th, trabecular thickness; Tb. Sp, trabecular separation; Tb. No, trabecular number; SMI, structural model index.
*$P < 0.05$,
**$P < 0.01$,
***$P < 0.001$ as compared to the OVX (vehicle) group.
$^a$ $P < 0.05$ where 100 mg/kg dose is significantly better as compared to 50 mg/kg dose.

Tibial trabecular data (table below) show that compared with the sham group, the OVx+vehicle group had significantly reduced BV/TV and Tb.No, and increased Tb.sp and SMI. Comparison of the A-4744/F004 treatment group with the OVx+vehicle group revealed significant increase in BV/TV and Tb.Th., and decrease in Tb.sp and SMI, suggesting that the microarchitectural features of the tibial trabecular bones are significantly protected by A-4744/F004 treatment of OVx rats.

treatment (12 weeks) and cultures prepared according to a previously published protocol (Maniatopoulos et al., 1988). Briefly, the femora were excised aseptically, cleaned of soft tissues, and washed 3 times, 15 min each, in a culture medium containing 10 times the usual concentration of antibiotics as mentioned above. The epiphyses of femora were cut and the marrow flushed out in 20 ml of culture medium consisting of α-MEM, supplemented with 15% fetal bovine serum, $10^{-7}$ M dexamethasone, 50 μg/ml ascor-

TABLE 3

μCT data of tibia after 12 weeks of treatment of OVx rats with A-4744/F004

| Trabecular Parameters (Tibia) | SHAM | OVX | 50 mg · kg$^{-1}$ · day$^{-1}$ | 100 mg · kg$^{-1}$ · day$^{-1}$ | ESTRADIOL (E2) 2.5 μg · kg$^{-1}$ · day$^{-1}$ |
|---|---|---|---|---|---|
| BV/TV (%) | 5.18 ± 0.63*** | 1.08 ± 0.18 | 1.68 ± 0.31 | 2.60 ± 0.21* $^a$ | 3.04 ± 0.24** |
| Tb. Th. | 0.097 ± 0.002 | 0.10 ± 0.003 | 0.11 ± 0.002 | 0.10 ± 0.004 | 0.10 ± 0.004 |
| Tb. Sp. | 1.02 ± 0.013*** | 1.42 ± 0.029 | 1.32 ± 0.044*** | 1.27 ± 0.011*** | 1.29 ± 0.029*** |
| Tb. No. | 0.77 ± 0.04*** | 0.13 ± 0.01 | 0.20 ± 0.03*** | 0.25 ± 0.02*** | 0.30 ± 0.02*** |
| SMI | 1.62 ± 0.088*** | 2.58 ± 0.078 | 2.25 ± 0.096*** | 2.21 ± 0.011** | 2.24 ± 0.021*** |

Values expressed as mean ± S.D. BV/TV, bone volume fraction; Tb. Th, trabecular thickness; Tb. Sp, trabecular separation; Tb. N, trabecular number; SMI, structural model index.
*$P < 0.05$,
**$P < 0.01$,
***$P < 0.001$ as compared to the OVX (vehicle) group.
$^a$ $P < 0.05$ where 100 mg/kg bodyweight dose is significantly better as compared to 50 mg/kg bodyweight.
$^b$$P < 0.05$ where 50 mg/kg bodyweight dose is significantly better as compared to 100 mg/kg bodyweight.

Evaluation of Estrogen Agonistic Effect

Figure 2:
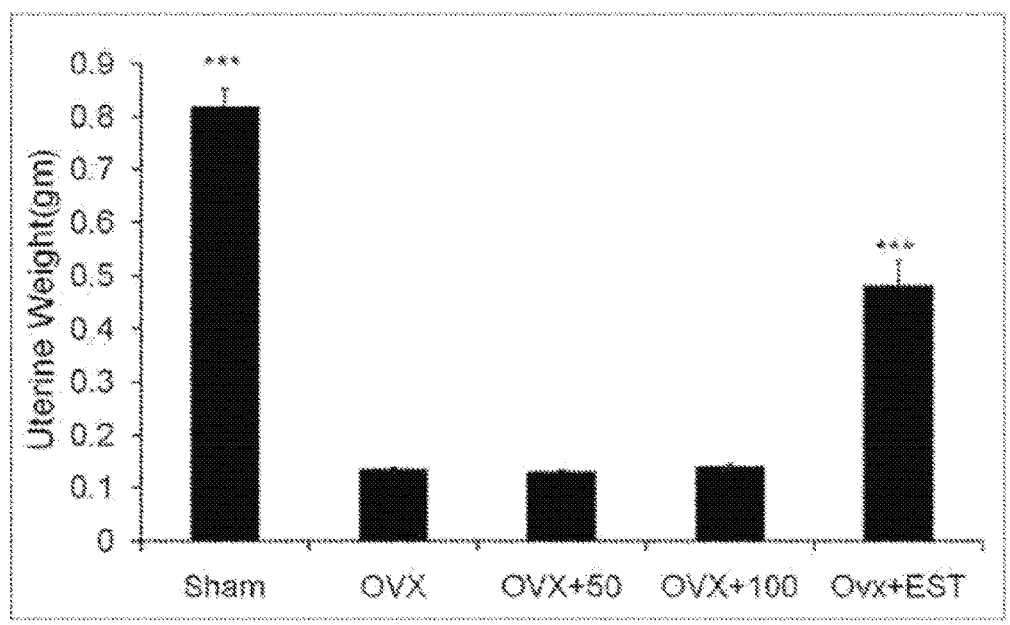
FIG. 2: Effect of A-4744/F004 extract on uterine weight

Estogenicity of the compound A-4744/F004 was evaluated in female Sprague Dawley rats. Figure represents the comparative data of the uterine weight of various groups including OVx and sham. It was observed that rats treated with the extract/compound had no estrogenic effect as uterine weights were comparable to OVx+vehicle group (see FIG. 2).

Measurement of Biochemical Parameters

Figure 3:
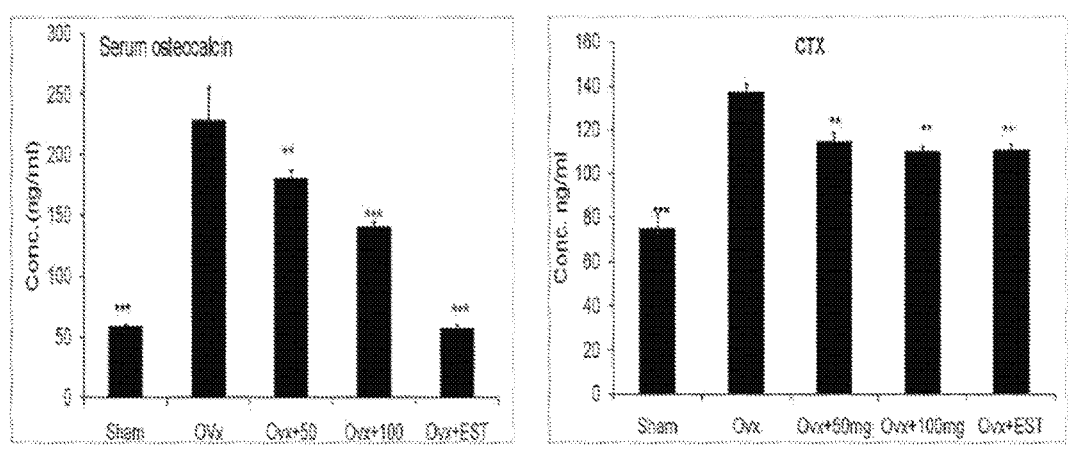
FIG. 3: Effect of A-4744/F004 on bone turnover markers, i.e serum osteocalcin and CTX
Figure 4A:
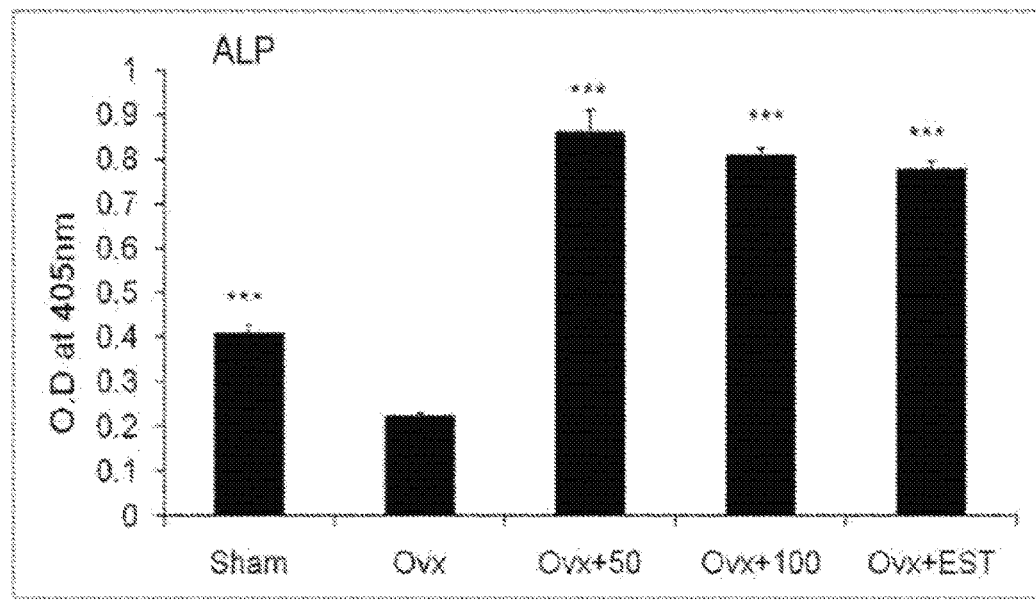
FIG. 4: ALP production (A) and mineralization (B, C) of BMCs in rats treated with A-4744/F004
Figure 4B:
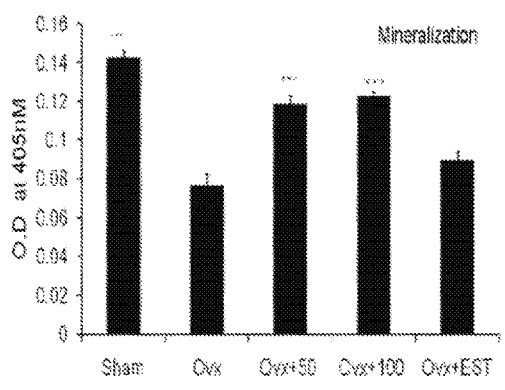
Figure 4C:
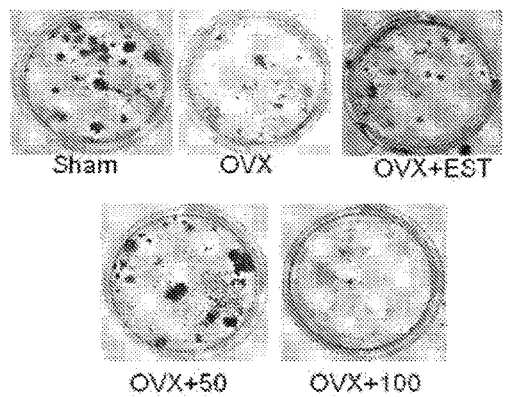

FIG. 3 shows that serum osteocalcin (assayed for more reliable mid portion of osteocalcin) and urinary CTX levels are elevated in OVx+vehicle group compared with sham+ vehicle group. Treatment of A-4744/F004 for 12 weeks to OVx rats resulted in significant reduction in the levels of both these bone turnover markers compared with OVx+ vehicle group. These data suggest that A-4744/F004 inhibits bone turnover rate that is characteristically elevated under estrogen deficiency.

bic acid, and 10 mM β-glycerophosphate. Released BMCs were collected and plated ($2 \times 10^6$ cells/well of 12-well plate for mineralization assay and $10^6$ cells/well of 48-well plate for ALP assay) in the culture medium, consisting of α-MEM, supplemented with 15% fetal bovine serum, $10^{-7}$M dexamethazone, 50 μg/ml ascorbic acid and 10 mM β-glycerophosphate. BMCs were cultured from the animals that were given treatment or otherwise for 11 days for ALP production and 21 days for mineralization, and the medium was changed every 48 h. After 21 days, the attached cells were fixed in 4% formaldehyde for 20 min at room temperature and rinsed once in PBS. After fixation, the specimens were processed for staining with 40 mM Alizarin Red-S, which stains areas rich in nascent calcium. Determination of ALP activity by osteoblast cells was done after 11 days of culture. Data show that A-4744/F004 treatment enhanced ALP production and mineralization by BMCs when compared with either OVx+vehicle or sham+vehicle groups (please see FIG. 4).

Dynamic Histomorphometry after Treatment with A-4744/F004

New bone formation during the period of administration of A-4744/F004 was assessed by double fluorochrome (tetracycline & calcein) labeling (representative photomicrograph below). FIG. 5 shows that there was no statistically significant change in mineral apposition rate (MAR) and bone formation rate (BFR) between OVx+vehicle, sham+vehicle groups in the femurs. On the other hand, treatment of OVx rats with A-4744/F004 resulted in significant increase in both MAR and BFR compared with other two groups.

Primary Osteoblast Cultures

Neonatal rat calvarial cell cultures are prepared as described previously (Chattopadhyay et al., Endocrinology 145:3451-62, 2004) using slight modification. Briefly, for calvarial osteoblast cultures, frontal and parietal bones from neonatal Sprague-Dawley rats (1-3 day old) were digested in 0.1% collagenase/0.1% dispase in α-MEM to obtain 5 sequential digests. The second through fifth digests are combined and grown to confluence at 37° C. and 5% $CO_2$ in air in α-MEM, supplemented with 10% fetal bovine serum (FBS), 2 mM glutamine, 100 U/ml penicillin-streptomycin, non-essential amino acid solution and sodium pyruvate. These osteoblast cells were further used to test thirteen pure compounds designated as 1-13. During the course of culture, pre-osteoblasts undergo three characteristic stages of osteoblasts with the expression of stage specific genes. These are:

Proliferation & differentiation: Days 1-12
  Genes—cbfa1, Osterix, Alkaline phosphatase, Collagen-1
Extra-cellular matrix maturation: Days 12-18
  Genes—Osteocalcin, Osteopontin, Fibronectin
Mineralization: Days 14-35
  Feature—Calcification (nodule formation)

Measurement of Osteoblast Alkaline Phosphatase (ALP) Activity

Figure 6:
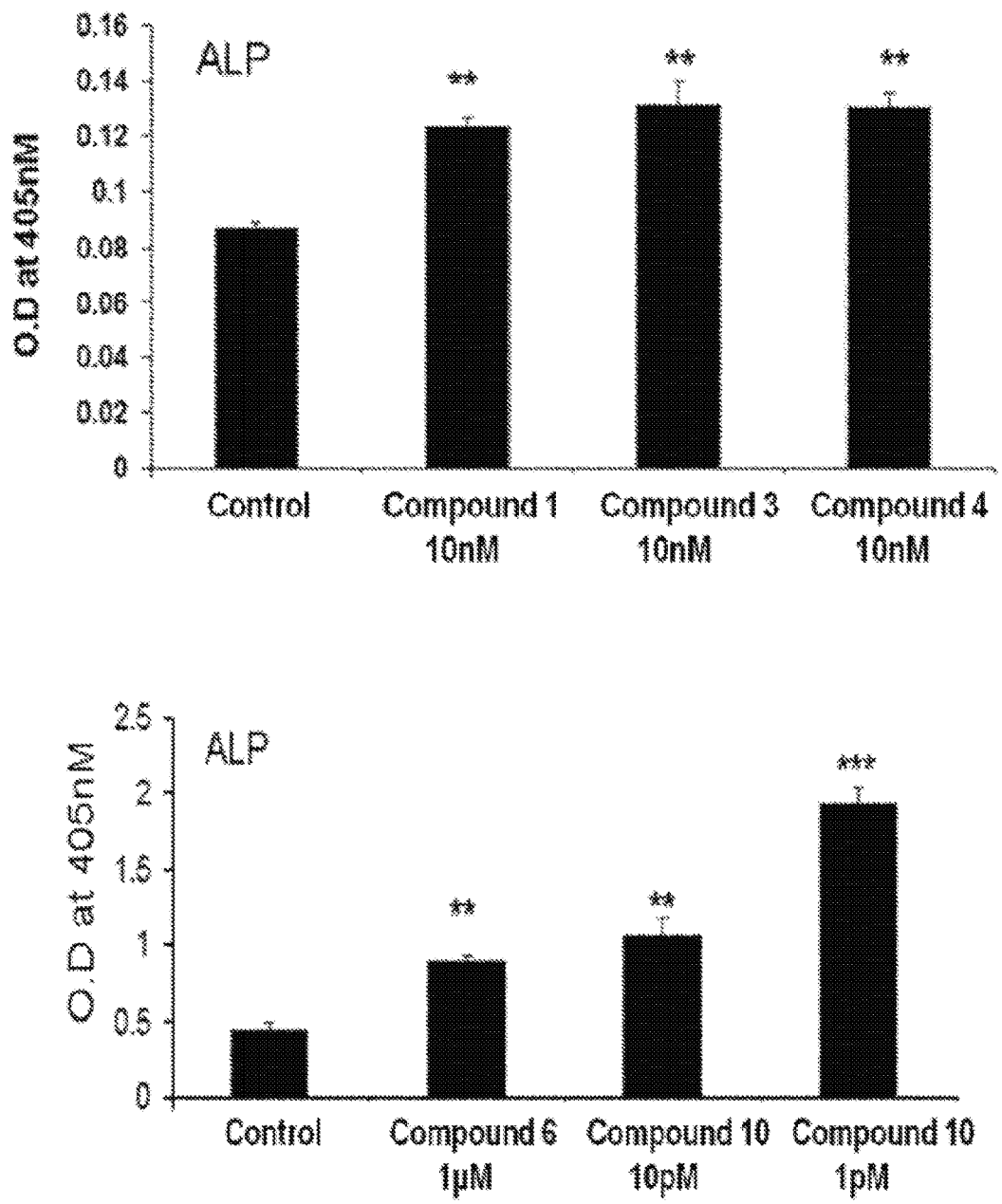
FIG. 6: Alkaline phosphatase activity of isolated pure compounds 1, 3, 4, 6 and 10 from the extract A-4744/F004

Calvarial osteoblasts cells were plated (1500 cells/well in 12 well plate) in the osteoblast differentiation medium and the culture was continued for 10 days with or without treatment with these compounds. This is the time when the ALP levels peak, and serves as an osteoblast differentiation marker. The cells at this point were washed twice with PBS and then plates were fixed by keeping them at −70° C. for 1 h, and then brought to room temperature to determine ALP activity. The rate of the reaction here is directly proportional to the enzyme activity, which itself is proportional to osteoblast differentiation. The O.D. was measured at 405 nm with a microplate reader. Out of all the compounds 1, 3, 4, 6 and 10 showed significantly increased ALP activity (FIG. 6).

Comparative In Vivo Osteogenic Efficacy Between Compound 4 and Compound 10

Ten 1- to 2-day-old rats were divided into two equal groups and given subcutaneous injection of either compound 4 or 10 (each 5.0 mg·kg$^{-1}$·day$^{-1}$ dose in 50 µl or equal volume of vehicle (normal saline, control) for 3 consecutive days. At the end of the treatment, pups were euthanized, individual calvaria harvested and cleaned of adherent tissue materials by gentle scrapping. Total RNA was isolated and qPCR for BMP-2 performed.

Figure 7:
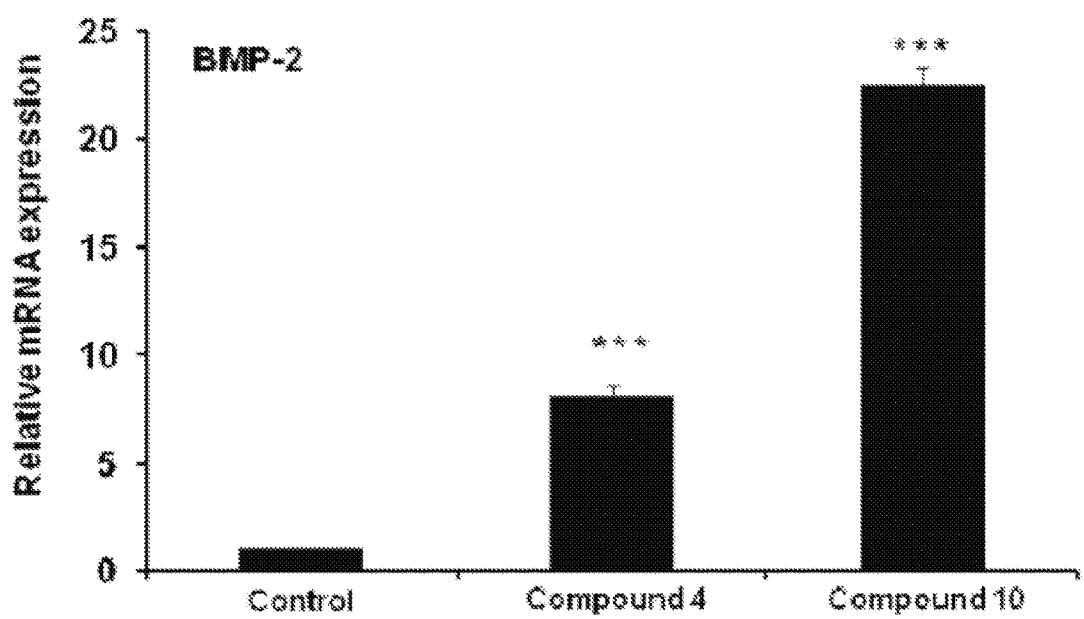
FIG. 7: Comparison of in vivo osteogenic efficacy between compound 4 and compound 10

For the comparison of osteogenic activity of the new compound 10, with compound 4, we studied the effect of compound 10 on the relative expression of the osteogenic gene, bone morphogenetic protein (BMP-2) in primary calvarial osteoblast cells by qPCR. The transcript levels of BMP-2 were significantly increased after treatment with both the compounds (p<0.001). Whereas compound 4 showed 5-fold increase in BMP-2 expression, compound 10 induced it by 15-folds. The results are expressed as fold change over untreated cells (FIG. 7).

Bioactive Compounds do not Cause Cell Growth Arrest

Figure 8:
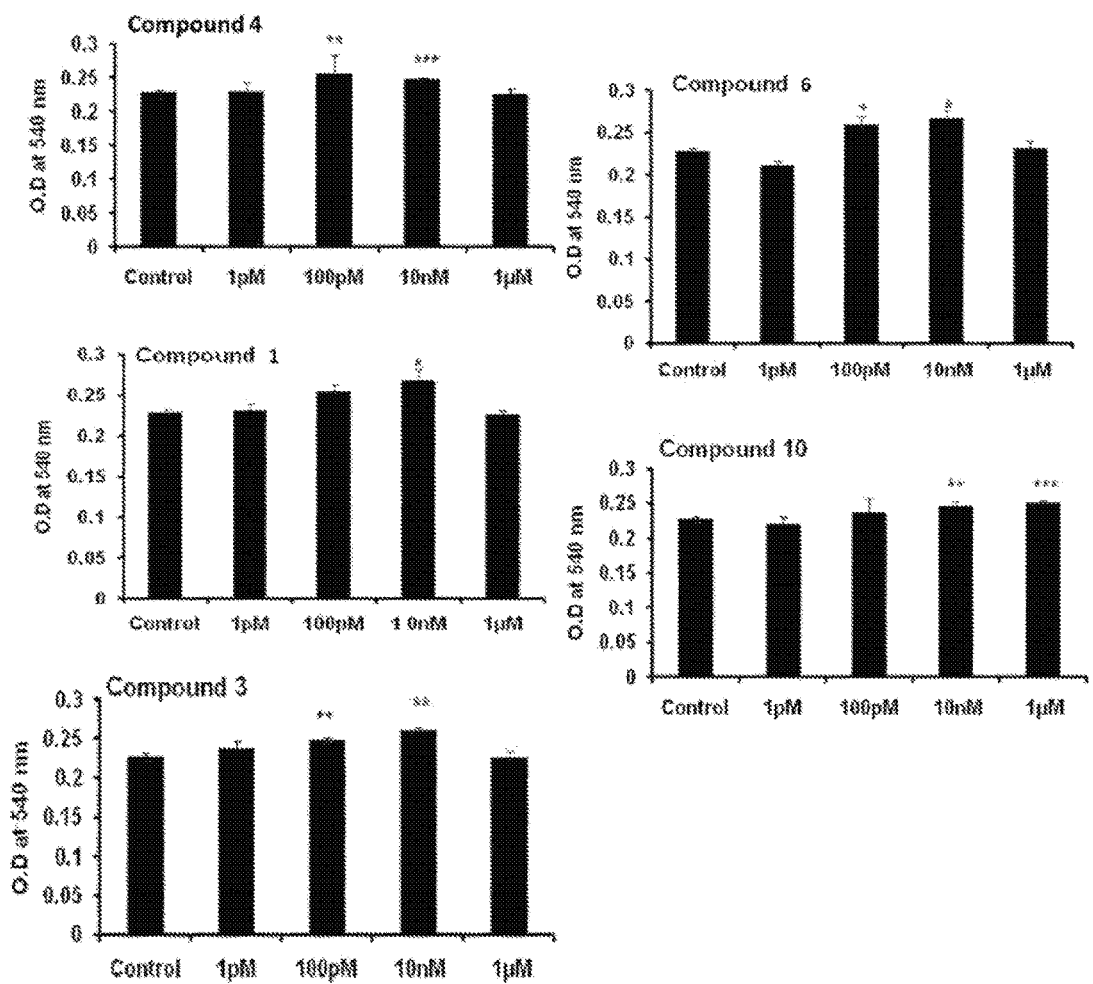
FIG. 8: Effect of the bioactive compounds 1, 3, 4, 6 and 10 on the proliferation of osteoblasts.

The ability of osteoblasts to replicate in the presence of the compounds (1, 3, 4, 6 and 10) is indicative of safety. Many isoflavonoids at micromolar concentrations are known to inhibit osteoblast cell growth. Osteoblasts were cultured in the absence or presence of compounds (dissolved in 0.01% DMSO final concentration) at various concentrations (1 pM to 1 µM) for 48 h. Cells receiving vehicle (0.01% DMSO) served as control. After incubation, the cells were washed with PBS. Then, cells were treated with MTT solution (5 mg/10 mL in DMEM devoid of Phenol Red) for 4 h. Formazon crystals formed were dissolved in DMSO and O.D. was taken at 540 nm. All the compounds were not toxic to the cells when compared to the control group, and they showed proliferation of the osteoblastic cells at some concentrations (FIG. 8).

In Vivo Treatment with Compound 10 the Active Constituent from A-4744/F004 of *Dalbergia Sissoo* in Ovariectomized Balb/c Mice The study was conducted in accordance with current legislation on animal experiments [Institutional Animal Ethical Committee (IAEC)] at C.D.R.I. Balb/c mice weighing ~25-30 gm were either bilaterally ovariectomized (OVx) or exposed to a sham surgical procedure. After ovariectomy, mice were left for 30 days for osteopenia to develop. Mice were individually housed at 21° C., in 12-h light:12-h dark cycles. All mice had excess to normal chow diet and water ad libitum. After 8 weeks, treatment in the form of gavage (1.0 mg and 5.0 mg/kg body weight) was given daily. Equal numbers of OVx and sham operated mice served as the control, and were given vehicle. At the end of 8 weeks, mice were euthanized. At autopsy, both femur and tibia were dissected and separated from adjacent tissue, cleaned, and used for µCT measurements.

As shown in the table below, OVx+vehicle group had significant microarchitectural deteriorations in the femur epiphysis as indicated by reduced BV/TV, Tb.Th and Tb.N compared with the sham group. Compound 10 treatment to OVx mice resulted in increased BV/TV, Tb.Th and Tb.N compared with OVx+vehicle group. Tb.sp and SMI were increased in OVx+vehicle group compared with sham, and compound 10 treatment to OVx mice increased both parameters compared to OVx+vehicle mice.

TABLE 4

µCT data of femur after 8 weeks of treatment of osteopenic mice with compound 10

| Trabecular Parameters (Femur) | SHAM | OVX | Comp 10 (1 mg · kg$^1$ · day$^1$) | Comp 10 (5 mg · kg$^1$ · day$^1$) |
|---|---|---|---|---|
| BV/TV (%) | 6.37 ± 0.28*** | 2.91 ± 0.152 | 4.10 ± 0.253** | 5.54 ± 0.739***$^a$ |
| Tb. Th. | 0.072 ± 0.002** | 0.059 ± 0.003 | 0.069 ± 0.002** | 0.070 ± 0.001** |

TABLE 4-continued

µCT data of femur after 8 weeks of treatment of osteopenic mice with compound 10

| Trabecular Parameters (Femur) | SHAM | OVX | Comp 10 (1 mg · kg$^1$ · day$^1$) | Comp 10 (5 mg · kg$^1$ · day$^1$) |
|---|---|---|---|---|
| Tb. Sp. | 0.445 ± 0.014*** | 0.618 ± 0.039 | 0.529 ± 0.022* | 0.502 ± 0.023 |
| Tb. No. | 1.029 ± 0.050*** | 0.444 ± 0.038 | 0.588 ± 0.034* | 0.759 ± 0.061***[b] |
| SMI | 1.834 ± 0.01077*** | 2.191 ± 0.0132 | 1.992 ± 0.0382*** | 1.615 ± 0.0434***[a] |

Values expressed as mean ± S.D. BV/TV, bone volume fraction; Tb. Th, trabecular thickness; Tb. Sp, trabecular separation; Tb. N, trabecular number; SMI, structural model index.
*$P < 0.05$,
**$P < 0.01$,
***$P < 0.001$ as compared to the OVX + vehicle group.
[a]$P < 0.001$,
[b]$P < 0.05$ where 5 mg/kg bodyweight dose is significantly better as compared to 1 mg/kg bodyweight.

In tibia metaphysis, compound 10 treatment significantly restored trabecular bone in OVx mice (table 5).

TABLE 5

µCT data of tibia after 8 weeks of treatment of osteopenic mice with comp 10

| Trabecular Parameters (Tibia) | SHAM | OVX | Comp 10 (1 mg · kg$^1$ · day$^1$) | Comp 10 (5 mg · kg$^1$ · day$^1$) |
|---|---|---|---|---|
| BV/TV (%) | 2.89 ± 0.198*** | 0.527 ± 0.106 | 1.67 ± 0.086*** | 1.701 ± 0.120*** |
| Tb. Th. | 0.065 ± 0.0009** | 0.057 ± 0.002 | 0.064 ± 0.0015* | 0.065 ± 0.001** |
| Tb. Sp. | 0.656 ± 0.017* | 0.755 ± 0.018 | 0.690 ± 0.013 | 0.671 ± 0.040 |
| Tb. No. | 0.487 ± 0.027*** | 0.164 ± 0.009 | 0.222 ± 0.018 | 0.266 ± 0.014* |
| SMI | 2.08 ± 0.055*** | 2.68 ± 0.057 | 2.46 ± 0.051*** | 2.43 ± 0.072*** |

Values expressed as mean ± S.D. BV/TV, bone volume fraction; Tb. Th, trabecular thickness; Tb. Sp, trabecular separation; Tb. N, trabecular number; SMI, structural model index.
*$P < 0.05$,
**$P < 0.01$,
***$P < 0.001$ as compared to the OVX + vehicle group.

Advantages of the Present Invention

A-4744/F004 has bone anabolic (i.e. new bone formation) effect rather than anti-resorptive (stopping further bone loss) effect of the majority of the anti-osteoporotic agents.

Unlike raloxifene, an agent of the present invention is devoid of uterine estrogenicity, which is an important safety parameter.

All the compounds exhibited no cytotoxicity on osteoblast cells as cell viability was comparable to the control cells (cells receiving vehicle).

We claim:

1. A method of prevention or treatment of a bone disorder, comprising administering to a subject in need thereof a pharmaceutical composition comprising an osteogenic effective amount of a purified compound of formula 10:

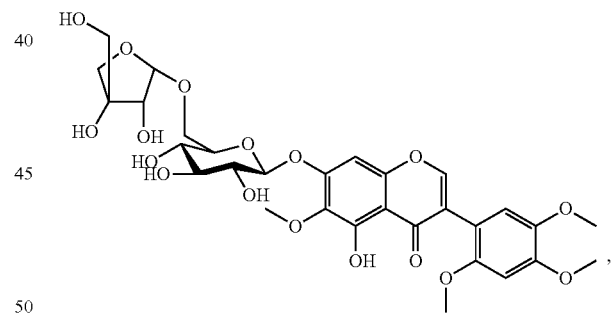

and pharmaceutically acceptable salts thereof, formulated in a tablet or capsule form with at least one pharmaceutically acceptable excipient,
wherein the bone disorder is a disease or condition caused by one or more of osteoporosis, bone loss, failure to achieve optimal bone formation, failure to achieve optimal bone fracture healing, low peak bone mass attainment during skeletal growth, and impaired new bone formation.

2. The method of claim 1, wherein the purified compound of formula 10 induces a 15-fold increase in bone morphogenic protein (BMP-2) expression in primary calvarial osteoblast cells in rats over that of vehicle-treated rats when administered at 5.0 mg·kg$^{-1}$·day$^{-1}$ for 3 consecutive days.

3. The method of claim 1, wherein the purified compound is non-toxic to primary calvarial osteoblast cells in rats when tested at concentration ranging between 1 pM to 1 μM for 48 h.

4. The method of claim 1, wherein the purified compound induces proliferation of primary calvarial osteoblast cells in rats when tested at a concentration ranging between 1 pM to 1 μM without causing cell growth arrest.

5. A method for prevention or treatment of bone disorders wherein the method comprises the steps of administering to a subject in need thereof a pharmaceutical composition comprising an osteogenic effective amount of a purified compound of formula 10

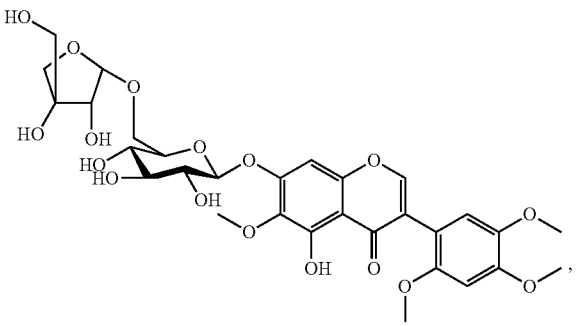

and pharmaceutically acceptable salts thereof in a tablet or capsule form formulated with a pharmaceutically acceptable excipient selected from one or more of lactose, mannitol, sorbitol, microcrystalline cellulose, sucrose, sodium citrate, and dicalcium phosphate.

6. A pharmaceutical composition comprising an osteogenic effective amount of a purified compound of formula 10,

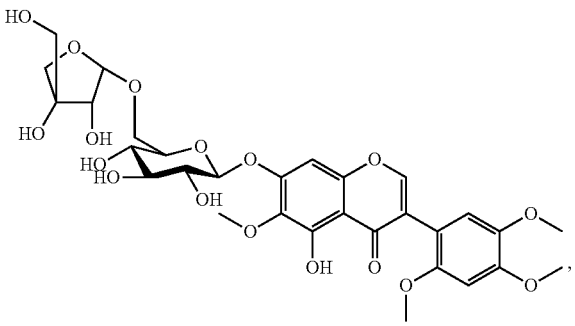

and pharmaceutically acceptable salts thereof, formulated in a tablet or capsule form.

7. The pharmaceutical composition as claimed in claim 6, wherein the purified compound exhibits a 15 fold increase when tested for bone morphogenic protein-2 expression in calvaria in rats over that of vehicle-treated rats at a dose of 5.0 mg kg$^{-1}$ day$^{-1}$ for 3 consecutive days.

8. The pharmaceutical composition as claimed in claim 6, wherein the purified compound is nontoxic to rat osteoblasts when tested at concentration ranging between 1 pM to 1 μM for 48 h.

9. The pharmaceutical composition as claimed in claim 6, wherein the purified compound induces proliferation of neonatal rat calvarial osteoblasts when tested at a concentration ranging from 1 pM to 1 μM without causing cell growth arrest.

10. The pharmaceutical composition as claimed in claim 6, wherein the purified compound exhibits an osteogenic effect when tested on bone marrow stromal cells at a concentration ranging from 1 mg/kg/day to 5 mg/kg/day.

11. The pharmaceutical composition as claimed in claim 6, wherein the purified compound is isolated from an n-butanol soluble fraction of an ethanol extract of leaves of a *Dalbergia sissoo* plant.

12. A pharmaceutical composition comprising a bone anabolically effective amount of a purified compound having formula 10

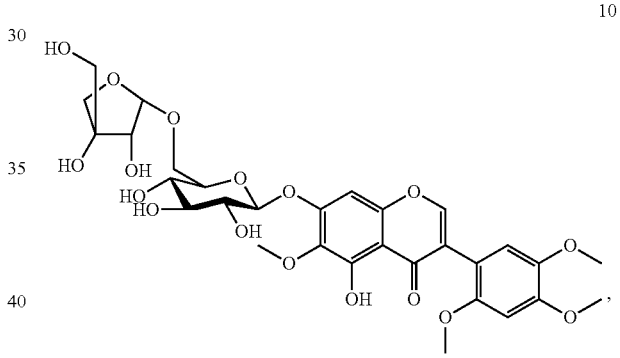

and pharmaceutically acceptable salts thereof, formulated in a tablet or capsule form with at least one pharmaceutically acceptable excipient.

13. A pharmaceutical composition as claimed in claim 12, wherein the pharmaceutically acceptable excipient is selected from the group consisting of lactose, mannitol, sorbitol, microcrystalline cellulose, sucrose, sodium citrate, dicalcium phosphate, and combinations thereof.

14. The pharmaceutical composition as claimed in claim 11, wherein the purified compound is isolated by chromatography from the n-butanol soluble fraction of the ethanol extract of the leaves of the *Dalbergia sissoo* plant.

* * * * *